(12) United States Patent  
Gestin et al.

(10) Patent No.: US 9,290,421 B2  
(45) Date of Patent: Mar. 22, 2016

(54) HYPERVALENT RADIOACTIVE ASTATINE OR IODINE COMPOUNDS, AND PREPARATION METHODS THEREOF

(75) Inventors: Jean-Francois Gestin, Nantes (FR); Francois Guerard, Nantes (FR); Alain Faivre-Chauvet, Nantes (FR)

(73) Assignees: Institut National de la Santé de la Recherche Medicalé, Paris (FR); Université de Nantes, Nantes (FR); CHU Nantes, Nantes (FR)

( * ) Notice: Subject to any disclaimer, the term of this patent is extended or adjusted under 35 U.S.C. 154(b) by 665 days.

(21) Appl. No.: 13/576,783

(22) PCT Filed: Feb. 2, 2011

(86) PCT No.: PCT/EP2011/051480  
§ 371 (c)(1),  
(2), (4) Date: Sep. 19, 2012

(87) PCT Pub. No.: WO2011/095517  
PCT Pub. Date: Aug. 11, 2011

(65) Prior Publication Data  
US 2013/0004420 A1     Jan. 3, 2013

(30) Foreign Application Priority Data  
Feb. 3, 2010   (EP) .................................. 10305110

(51) Int. Cl.  
| | |
|---|---|
| *A61K 51/00* | (2006.01) |
| *A61M 36/14* | (2006.01) |
| *C07B 59/00* | (2006.01) |
| *C07C 213/00* | (2006.01) |
| *C07C 213/02* | (2006.01) |
| *C07D 347/00* | (2006.01) |
| *C07D 421/12* | (2006.01) |
| *C07F 7/22* | (2006.01) |

(52) U.S. Cl.  
CPC ............. *C07B 59/002* (2013.01); *C07C 213/00* (2013.01); *C07C 213/02* (2013.01); *C07D 347/00* (2013.01); *C07D 421/12* (2013.01); *C07F 7/2212* (2013.01)

(58) Field of Classification Search  
CPC ..... A61K 51/00; A61K 51/04; A61K 51/041; C07D 347/00; C07D 421/12; C07B 59/002; C07C 213/00; C07C 213/02; C07C 215/68; C07C 217/48; C07F 7/2212  
USPC .......... 424/1.11, 1.61, 1.65, 1.77, 1.81, 1.85, 424/1.89, 9.1, 9.3, 9.37, 9.45; 514/1, 19.2, 514/19.3  
See application file for complete search history.

(56) References Cited

U.S. PATENT DOCUMENTS 4,279,887 A     7/1981   Baldwin et al.

FOREIGN PATENT DOCUMENTS

| DE | 268699 A1 | 6/1989 |
|---|---|---|
| JP | 2003231635 A | 8/2003 |

OTHER PUBLICATIONS

C. C. Huang et al. "Potential Organ- or Tumor-Imaging Agents. 18. Radionated Diamines and Bisquaternaries", J. Med. Chem., 1979, pp. 449-452, vol. 22, No. 4.  
Metallinos et al., "N-Cumyl Benzamide, Sulfonamide, and Aryl O-Carbamate Directed Metalation Groups. Mild Hydralytic Lability for Facile Manipulation of Directed Ortho Metalation Derived Aromatics" Organic Letters, 1999, vol. 1, No. 8, p. 1183-1186.  
Srivastava et al., "Synthesis and Myocardial Specificity of p-(n-alkyl)-[125I]—Iodophenyl Fatty Acid Analogues" Indian Journal of Chemistry, 1991, vol. 30B, p. 188-194.  
STN Database Caplus, 1989, AN:1989:492873, DN:111:92873, Radiologia Lugoslavica, 1989, 23(2), p. 173-174.  
Stanko et al., "Copper Catalysis on Isotopic Exchange as a Novel Approach to Incorporating Iodine and Bromine into Benzene Derivatives", International Journal of Applied Radiation and Isotopes, 1984, vol. 35, No. 12, p. 1129-1132.  
Khimicheskaia Fizika, 1983, vol. 3, p. 362-369 (non-English document).  
STN Database CAPLUS, 1983, AN: 1983:528430, DN:99:128430, Nukleon, 1983, vol. 1, p. 16-19.

(Continued)

*Primary Examiner* — D L Jones  
(74) *Attorney, Agent, or Firm* — Whitham, Curtis, Christofferson & Cook, P.C.

(57) ABSTRACT

The present invention relates to a compound having formula (I): wherein: —X is in particular $^{125}$I Or $^{211}$At; —$R_1$ and $R'_1$ are independently from each other chosen preferably from the group consisting of electron-withdrawing groups and alkyl groups; —$R_2$ is chosen from the group consisting of: H, alkyl groups, functional groups being able to bind a vector, and functional groups having targeting properties which make the compound of the invention a vector itself; —Z is a heteroatom, $R_5$, $R_8$ and $R_9$ are preferably H; —Y is preferably an electron withdrawing group.

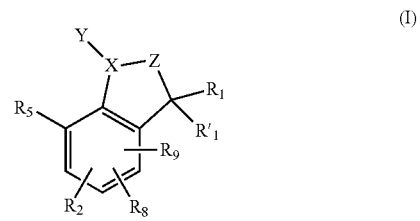

(I)

15 Claims, No Drawings

(56) References Cited

OTHER PUBLICATIONS

Visser et al., "The Synthesis of Organic At-Compounds Through Thallium Compounds", International Journal of Applied Radiation and Isotopes, 1982, vol. 33, p. 389-390.

Baldwin et al., "Structure-Activity Relationships of 123I Labeled o-Iodobenzamide Derivatives" Journal of Radioanalytical Chemistry, 1981, vol. 65, No. 1-2, p. 269-277.

STN Database Registry, 1984, CAS No. 23064-23-5.

Amey et al., "Synthesis and Reaction of Substituted Arylalkoxyiodinanes: Formation of Stable Bromoarylalkoxy and Aryldialkoxy Heterocyclic Derivatives of Tricoordinate Organoiodine (III)" Journal of Organic Chemistry, 1979, vol. 44, No. 11, p. 1779-1784.

Nguyen et al., "Tridentate Ligand Useful in Stabilizing Higher Coordination States of Nonmetallic Elements. An Aryldialkoxydifluoroperiodinane", Journal of Organic Chemistry, 1982, vol. 47, p. 1024-1027.

HYPERVALENT RADIOACTIVE ASTATINE OR IODINE COMPOUNDS, AND PREPARATION METHODS THEREOF

CROSS-REFERENCE TO RELATED APPLICATIONS

This application is a national stage patent filing under 35 U.S.C. 371 of International patent application PCT/EP2011/051480 filed 2 Feb. 2011.

The present invention concerns hypervalent radioactive astatine or iodine compounds, as well as preparation methods thereof.

Astatine-211 is a promising radionuclide for targeted alpha-therapy, which allows high radiation dose in small tumour volume while not affecting the surrounding healthy tissues. In association with a suited tumor-targeting biomolecule, its radiophysical properties make it one of the best candidates for the treatment of small disseminated cancers. Particularly, its physical half-life (7.21 h) is adapted to the pharmacokinetics of biomolecules to be labeled for radiotherapy (Zalutsky M R, Vaidyanathan G (2000) *Curr Pharm Des.* 6; 1433-1455). It is produced by bombardment of alpha particles on bismuth-209 via the Bi-209($\alpha$,2n)At-211 nuclear reaction.

Astatine is the heaviest halogen. Because there is no stable isotope of this element and because the longest-lived has only an 8.1 h half-life (At-210), its chemistry is not fully understood. Only few cyclotrons can produce astatine-211, that is why iodine radioisotopes are generally used to study and predict astatine reactivity before its use (particularly iodine-125 which is easily available). Indeed, because iodine is the nearest element in terms of chemical properties, some similarities are observed. But in many aspects, noticable differencies are highlighted (e.g. metallic properties for astatine) which show that preliminary results obtained with iodine must be considered with reserve as astatine can behave differently in similar conditions.

Several oxidation states of astatine have been established (−1, 0, +1, +3, +5, +7). For biomolecule labelling, At-211 is generally linked to the vector in the +1 oxidation state (Aromatic carbon-astatine (Zalutsky M R, Pradeep K. Garg, Henry S. Friedman, and Darell D. Bigner (1989) *Proc. Natl. Acad. Sci. U.S.A*, 86, 7149-7153) or boron-astatine bond (Wilbur D S, Chyan M K, Hamlin D K, Perry M A. (2009) *Bioconjugate Chem.* 20; 591-602)) and less frequently in the −1 oxidation state (e.g. metal-astatine bond) (Pruszyński M, Bilewicz A, Zalutsky M R (2007) *Bioconjugate Chem.* 19; 958-965).

Astatine-211 is considered for targeted radionuclide therapy of various cancers after conjugation to a molecular vector. However deastatination of the molecular vector labeled with this atom has been observed in vivo, leading to non-specific irradiation of healthy organs. Improved labeling methods remain necessary to increase the stability of the astatine bond to its vector.

The labeling methods developed for astatine can find applications with radioactive isotopes of iodine also. The most considered isotope for therapy is iodine-131. It is a beta particle emitter with a 8 days half-life decaying to the stable xenon-131. In association with suitable vectors, iodine-131 has already found clinical applications for cancer therapies (Macklis M R (2006) *Int. J. Radiation Oncology Biol. Phys.* 66; S30-S34). Iodine-125 which is easily available is generally used for preliminary radiolabeling tests before the use of the more expensive isotopes cited above. But its use is considered for therapy regarding its extremely short auger electron emission especially when linked to a cell internalizing vector (Meredith M R et al (1995) *J. Nucl. Med.* 36; 2229-2233).

Iodine-123 and iodine-124 represent the most useful iodine isotopes for cancer detection. With a 13.2 h half-life and gamma decay, iodine-123 is suitable for various diagnostic by gamma camera detection (Bourguignon M H, Pauwels E K J, Loc'h C, Mazière B (1997) *Eur. J. Nucl. Med.* 24; 331-344). Iodine-124 decays by positron emission with a 4,2 day half-life. It can be used as a tracer in positron emission tomography (PET) (Pentlow K S et al (1996) *J. Nucl. Med.* 37; 1557-1562).

The object of the present invention is to provide astatine or iodine compounds that allow labeled biomolecules to remain labeled and bind specific organs to be detected or irradiated by using the radiohalogen linked in a stabilised +3 oxydation state.

The present invention thus relates to a compound having formula (I):

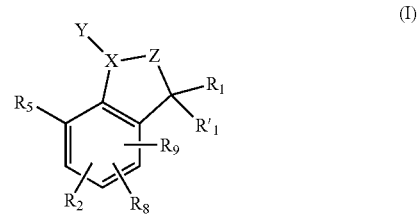

wherein:

X is a radioisotope chosen from the group consisting of: $^{125}I$, $^{123}I$, $^{124}I$, $^{131}I$, and $^{211}At$;

$R_1$ and $R'_1$, are independently from each other chosen from the group consisting of electron-withdrawing groups and alkyl groups, preferably at least one of $R_1$ and $R'_1$ being an electron-withdrawing group, or $R_1$ and $R'_1$ may form together with the adjacent carbon atom carrying them a C=O group;

$R_2$ is chosen from the group consisting of: H, alkyl groups, functional groups being able to bind a vector, and functional groups having targeting properties which make the compound of the invention a vector itself;

$R_8$ and $R_9$ are independently from each other chosen from the group consisting of H, OH, $NH_2$, halogen, alkyl groups, alkoxy groups, amine groups, amide groups, and ester groups;

Z is a heteroatom, in particular selected from the group consisting of: O and NH, $R_5$ is H or is a —$C(R_6)(R_7)$— radical forming together with Y and X a five-membered heterocycle when Y is a heteroatom having the same definition as Z, $R_6$ and $R_7$ being as defined above for $R_1$ and $R'_1$; and Y is an electro-attractive group, in particular Br, Cl, F, or OAc, or Y is an heteroatom Z forming a five-membered heterocycle together with X and $R_5$ being a radical —$C(R_6)(R_7)$—.

The term electron-withdrawing group is recognized in the art and denotes the tendency of a substituent to attract valence electrons from neighbouring atoms, i.e., the substituent is electronegative with respect to neighbouring atoms. A quantification of the level of electron-withdrawing capability is given by the Hammett sigma ($\sigma$) constant. This well known constant is described in many references, for instance, J. March, Advanced Organic Chemistry, McGraw Hill Book Company, New York, (1977 edition) pp. 251-259. The Hammett constant values are generally negative for electron donating groups ($\sigma[P]=-0.66$ for $NH_2$), $\sigma[P]$ indicating para substitution. Exemplary electron-withdrawing groups include nitro, acyl, formyl, sulfonyl, trifluoromethyl, cyano, chloride, and the like.

The term "alkyl" means a saturated or unsaturated aliphatic hydrocarbon group which may be straight or branched having 1 to 12 carbon atoms in the chain. Preferred alkyl groups have 1 to 6 carbon atoms in the chain. "Branched" means that one or lower alkyl groups such as methyl, ethyl or propyl are attached to a linear alkyl chain. <<Lower alkyl>>, means 1 to 4 carbon atoms in the chain which may be straight or branched. The alkyl may be substituted with one or more <<alkyl group substituants>>, which may be the same or different, and include for instance halo, cycloalkyl, hydroxy, alkoxy, amino, acylamino, aroylamino, carboxy.

The expression "functional groups being able to bind a vector" refers to a chemical group which is reactive towards the chemical functions of a vector and thus allows the formation of a stable chemical bond between the vector and the synthon (which is the compound of formula (I)).

Among such functional groups, the followings may be cited: maleimide, activated ester (e.g. N-hydroxysuccinimide, tetrafluorophenyl ester), isothiocyanate, isocyanate, anhydride, or any reactive groups for "click chemistry" such as alkyne or azide groups.

The term "vector" refers to a molecule being able to recognize a biological target tissue (depending on the pathology to be treated or detected). In particular, this term may refer to an antibody or fragments thereof or any antibody construct (like minibodies, diabodies etc. . . . resulting of antibody engineering), as well as a hapten, a peptide or a drug, or a nanocarrier compound able to recognize the target cells such as a nanocapsule, a liposome, a dendrimer or a carbon nanotube. These nanocarriers may be linked if necessary to tumor specific ligands.

More preferably, this term may refer to organic compounds binding cells or organic compounds transported by transporters expressed by cells (e.g. but not limited to glucose, aminoacids, biogenic amines), peptides binding specific receptors (e.g. but not limited to somatostatine, cholecystokinine, neurotensine receptors), haptens, proteins (e.g. but not limited to antibodies, antibody fragments and their derivatives, recombinant proteins or synthetic peptides selected to bind target cells (e.g. but not limited to affibodies)).

The term "alkoxy" refers to an —O-alkyl radical.

The term "halo" (or "Hal") refers to the atoms of the group 17 of the periodic table (halogens) and includes in particular fluorine, chlorine, bromine, and iodine atom.

In formula (I) above, the groups $R_6$ and $R_7$ may be identical or different and they also may be identical to or different from the groups $R_1$ and $R'_1$.

Preferably, in formula (I), $R_8$ and $R_9$ are H.

Particular compounds of the invention have the following formula (I-1-1):

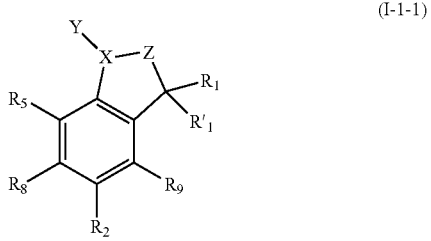

wherein X, Y, Z, $R'_1$, $R_1$, $R_2$, $R_5$, $R_8$ and $R_9$ are as defined above in formula (I), $R_1$ and $R'_1$ being preferably identical. Preferably, in formula (I-1-1), $R_8$ and $R_9$ are H.

The present invention also relates to a compound having formula (I-1-2) or (I-1-3):

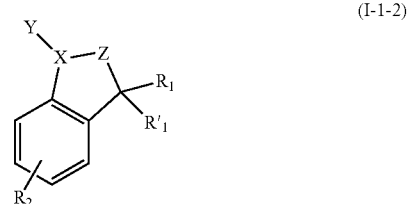

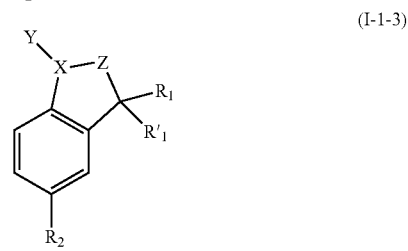

wherein X, Y, Z, $R'_1$, $R_1$ and $R_2$ are as defined above in formula (I), $R_1$ and $R'_1$ being preferably identical.

Preferably in formulae (I-1-2) and (I-1-3), Z is O.

In formulae (I-1-2) and (I-1-3), Y is an electron-withdrawing group.

The present invention also relates to a compound having formula (I'):

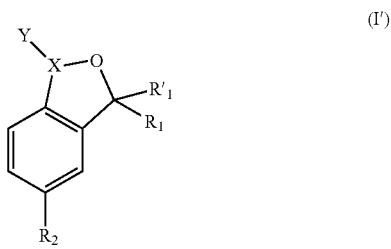

wherein X, Y, $R'_1$, $R_1$ and $R_2$ are as defined above in formula (I), $R_1$ and $R'_1$ being preferably identical, and X being preferably $^{125}I$ or $^{211}At$.

The present invention also relates to a compound having formula (I"):

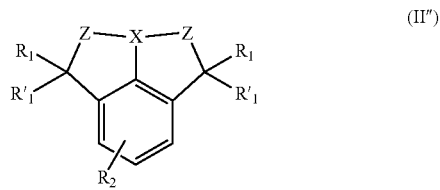

wherein X, Z, $R'_1$, $R_1$ and $R_2$ are as defined above in formula (I), $R_1$ and $R'_1$ being preferably identical.

In formula (I"), X is preferably $^{125}I$ or $^{211}At$.

In the above formulae, $R'_1$ is preferably an electron-withdrawing group and $R_1$ is preferably an alkyl group or an electron-withdrawing group.

In the above formulae, $R_2$ may also represent a group having targeting properties which make the compound of the invention a vector itself such as biotine and derivatives thereof.

In particular, $R_2$ may represent maleimide, N-hydroxysuccinimide, isothiocyanate, isocyanate, anhydride, or a group of formula:

The present invention also relates to compounds having formula (I-1):

(I-1)

wherein X, $R'_1$, $R_1$ and $R_2$ are as defined above in formula (I), $R_1$ and $R'_1$ being preferably identical.

Another group of compounds of the invention consists of compounds having formula (I-2):

(I-2)

wherein X, $R'_1$, $R_1$ and $R_2$ are as defined above in formula (I), $R_1$ and $R'_1$ being preferably identical.

Preferably, in formulae (I), (I-1) or (I-2), $R_1$ and $R'_1$ are chosen from the group consisting of: fluorinated alkyl groups such as $-CF_3$ or $-CF_2-CF_3$, $-CCl_3$, $-OH$, $-NH_2$, and $-NO_2$.

According to an advantageous embodiment, in formulae (I), (I-1) or (I-2), $R_1$ and $R'_1$ are $CF_3$.

According to another advantageous embodiment, in formulae (I), (I-1) or (I-2), $R_2$ is an alkyl group, and preferably a methyl group.

A particular group of compounds according to the invention consists of compounds having one of the following formulae (I-3), (I-4), (I-5), (I-6), (I-7) and (I-8):

(I-3)

(I-4)

(I-5)

(I-6)

(I-7)

(I-8)

X and Y being as defined above in formula (I), and $R'_2$ being an alkyl group as defined above.

According to an advantageous embodiment, in formulae (I), (I-1), (I-2), (I-3), (I-4), (I-5), (I-6), (I-7) and (I-8), X is $^{125}I$.

According to another advantageous embodiment, in formulae (I), (I-1), (I-2), (I-3), (I-4), (I-5), (I-6), (I-7) and (I-8), X is $^{211}At$.

The astatine compounds of the invention are labeled with hypervalent astatine at +3 oxidation state. They are very stable as the astatine atom is bonded to three atoms by covalent bonding (whereas the known astatine compounds contain only one bond: astatine at +1 oxidation state).

Such compounds are designed to increase the stability of the hypervalent bonds: the astatine atom is included in a five-membered ring, the formation of which being promoted by the gem-dialkyl effect of the $CF_3$ groups. Furthermore, the astatine atom is bonded to electronegative atoms in apical position in order to obtain a maximal increase of the chemical stability.

The present invention relates to the following specific compounds:

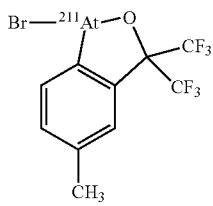
(I-9)

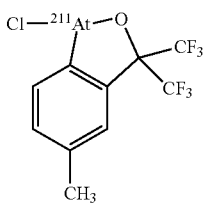
(I-10)

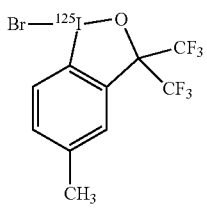
(I-11)

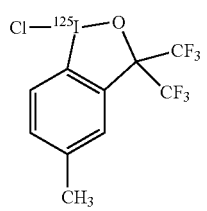
(I-12)

The present invention also relates to compounds having formula (II):

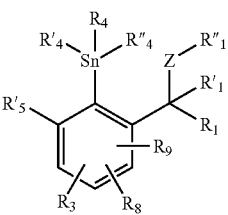
(II)

wherein:
Z, $R_1$, $R'_1$, $R_8$ and $R_9$ are as defined above in formula (I);
$R''_1$ is chosen from H and protective groups;
$R'_5$ is H or is a —$C(R_6)(R_7)(ZR_{10})$ group, $R_6$ and $R_7$ being as defined above in formula (I), Z being as defined above, and $R_{10}$ being chosen from H and protective groups; and
$R_2$ is chosen from the group consisting of: H, alkyl groups, functional groups being able to bind a vector, and functional groups having targeting properties which make the compound of the invention a vector itself;
$R_4$, $R'_4$ and $R''_4$ are chosen independently from each other from the group consisting of alkyl groups and aryl groups.

Preferably, in formula (II), $R_8$ and $R_9$ are H.
Preferably, in formula (II), $R''_1$ is a protective group, such as a methoxymethyl ether group.

The present invention also relates to compounds having formula (II') or (II''):

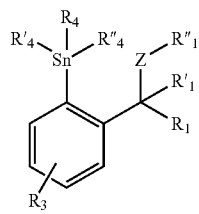
(II')

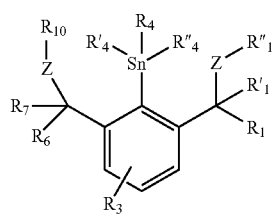
(II'')

$R_3$, $R_4$, $R'_4$, $R''_4$, $R_1$, $R'_1$, $R''_1$, Z, $R_6$, $R_7$ and $R_{10}$ being as defined above.

Preferably, in formulae (II), (II') and (II''), Z is O.

These compounds are intermediate compounds which are used to prepare the compounds of the invention having formula (I).

The term "protective group" or "protecting group" means a substituent which protects groups, in particular hydroxyl groups, against undesirable reactions during synthetic procedures. Examples of protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used protecting groups are disclosed in T. W. Greene and P. G. M. Wuts, Protective Groups in Organic Synthesis, 3rd edition, John Wiley & Sons, New York (1999).

The term "aryl" refers to an aromatic monocyclic, bicyclic, or tricyclic hydrocarbon ring system, wherein any ring atom capable of substitution may be substituted by a substituent. Examples of aryl moieties include, but are not limited to, phenyl, naphthyl, and anthracenyl.

The preferred substituents on aryl groups are amino, amine, alkoxy, halo, perfluoroalkyl such as $CF_3$, heterocyclyl, amide, and ester.

In formulae (II), (II') and (II") above, the groups $R_1$ and $R'_1$ may be identical or different and the groups $R_6$ and $R_7$ may be identical or different. The groups $R_6$ and $R_7$ may also be identical to or different from the groups $R_1$ and $R'_1$.

According to an advantageous embodiment of the present invention, in formulae (II), (II') and (II"), $R''_1$ is a MOM group (methoxymethyl ether).

According to an advantageous embodiment of the present invention, in formulae (II), (II') and (II"), $R_4$, $R'_4$ and $R''_4$ are chosen from methyl or butyl. Preferably, $R_4$, $R'_4$ and $R''_4$ are identical and represent methyl or butyl.

According to an advantageous embodiment of the present invention, in formulae (II), (II') and (II"), $R_3$ is chosen from the following groups:

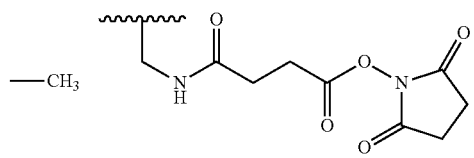

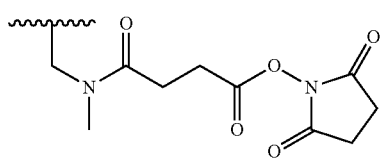

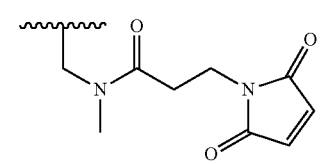

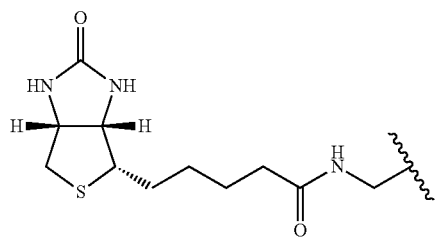

The present invention also relates to compounds having formula (I'-1) or (I"-1):

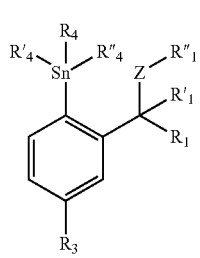

(II'-1)

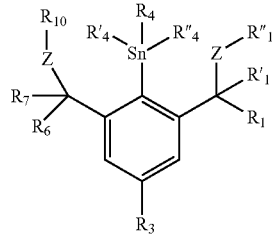

(II"-1)

$R_3$, $R_4$, $R'_4$, $R''_4$, $R_1$, $R'_1$, $R''_1$, Z, $R_6$, $R_7$ and $R_{10}$ being as defined above.

Preferred compounds of the invention having formula (II) are compounds having one of the following formulae (I'-1) or (I-2):

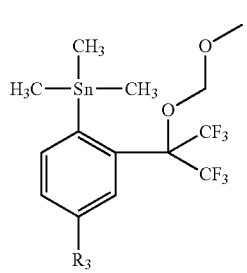

(II-1)

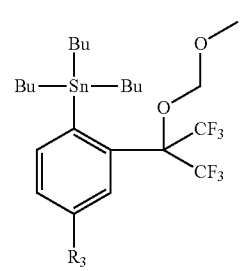

(II-2)

$R_3$ being as defined above.

The present invention also relates to the following specific intermediate compounds:

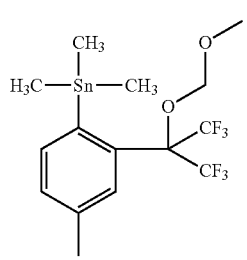

(II-3)

-continued

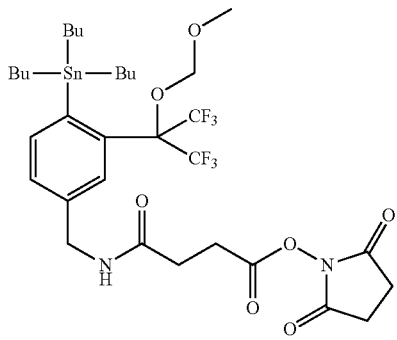
(II-4)

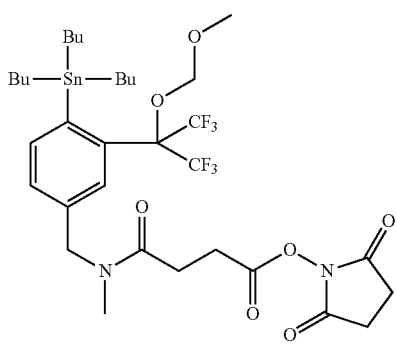
(II-5)

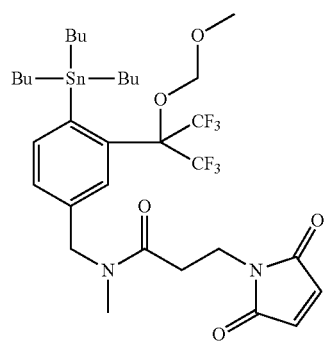
(II-6)

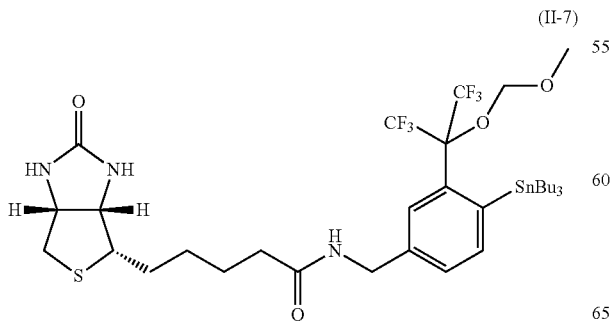
(II-7)

The present invention also relates to compounds having formula (III):

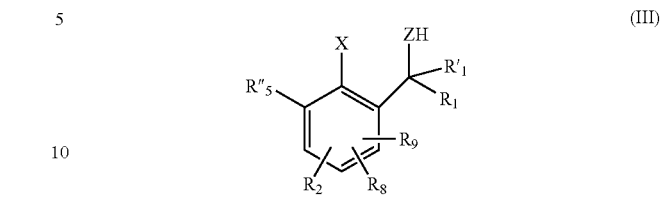
(III)

wherein Z, X, $R_1$, $R'_1$, $R_2$, $R_8$ and $R_9$ are as defined above in formula (I), and $R''_5$ is H or a —$C(R_6)(R_7)(ZH)$ group, $R_6$ and $R_7$ being as defined above in formula (I).

Preferably, in formulae (III), $R_8$ and $R_9$ are H.

The present invention also relates to compounds having formula (III') or (III"):

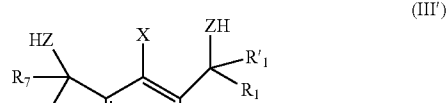
(III')

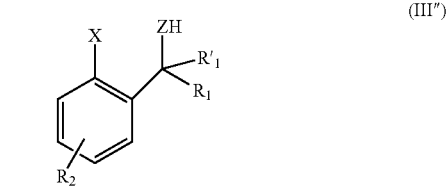
(III")

X, $R_2$, $R_1$, $R'_1$, Z, $R_6$, and $R_7$ being as defined above.

The present invention also relates to compounds having formula (III'-1) or (III"-1):

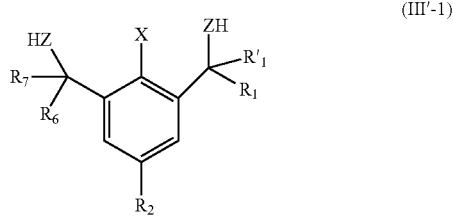
(III'-1)

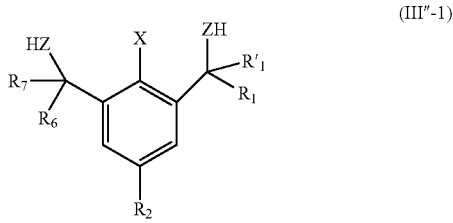
(III"-1)

Preferably, in formulae (III), (III'), (III"), (III'-1) and (III"-1), Z is O.

In formulae (III), (III'), (III"), (III'-1) and (III"-1) above, the groups $R_1$ and $R'_1$ may be identical or different and the groups $R_6$ and $R_7$ may be identical or different. The groups $R_6$ and $R_7$ may also be identical to or different from the groups $R_1$ and $R'_1$.

These compounds are intermediate compounds which are used to prepare the compounds of the invention having formula (II).

According to an advantageous embodiment, in formula (III), (III'), (III"), (III'-1) and (III"-1), $R_1$ and $R'_1$ are $CF_3$.

According to another advantageous embodiment, in formula (III), (III'), (III"), (III'-1) and (III"-1), $R_2$ is an alkyl group, and preferably a methyl group.

The present invention also relates to the following specific intermediate compounds:

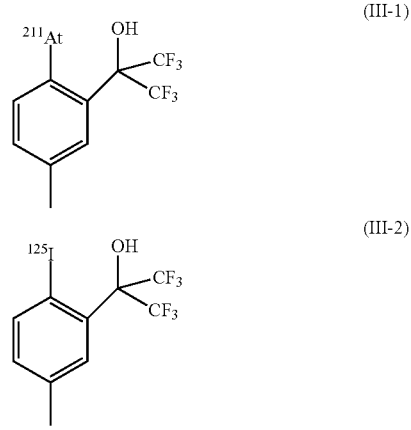

The present invention also relates to a method for the preparation of a compound having formula (I) as defined above, comprising the reaction of an halogenation agent with a compound of formula (III) as defined above.

The expression "halogenation agent" designates a reactant useful to introduce a halogen group, such as Br or Cl, in a given molecule.

Among halogenation agents, one may cite the following agents: HCl/NaOCl, N-bromosuccinimide (NBS), $Cl_2$, $Br_2$ or tBuOCl, $SO_2Cl_2$, $PCl_5$, $CBr_4$, and $PBr_3$.

The present invention also relates to a method for the preparation of a compound having formula (I-1) as defined above, comprising the reaction of a bromation agent chosen from N-bromosuccinimide, $Br_2$ $CBr_4$, and $PBr_3$, with a compound of formula (III) as defined above.

Preferably, this bromation step is carried out in a solvent preferably chosen from: propan-2-ol, methanol, chloroform or acetonitrile.

According to a preferred embodiment, this step is carried out for 5 minutes to 120 minutes, and preferably for 30 minutes.

According to a preferred embodiment, this step is carried out at a temperature of 20° C. to 150° C., and preferably at 60° C.

The present invention also relates to a method for the preparation of a compound having formula (I-2) as defined above, comprising the reaction of a chlorination agent chosen from $Cl_2$, tBuOCl, $SO_2Cl_2$, $PCl_5$ and a mixture of hydrochloric acid and sodium hypochlorite with a compound of formula (III) as defined above.

According to a preferred embodiment, the chlorination step is carried out for 5 minutes to 120 minutes, and preferably for 30 minutes.

According to a preferred embodiment, the chlorination step is carried out at a temperature of 20° C. to 150° C., and preferably at 60° C.

According to an advantageous embodiment, the compound having formula (III) is prepared by halodestannylation and radiolabeling of a compound of formula (II) as defined above.

This method thus allows the leaving of a tin group followed by the introduction of an iodine or astatine atom.

According to a preferred embodiment, the present invention relates to the preparation of a compound of formula (III) wherein X is iodine, by halodestannylation and radioiodination of a compound of formula (II) as defined above. Such compounds of formula (III) are used then to prepare compounds of formula (I) as defined above wherein X is iodine.

This embodiment is preferably carried out in MeOH/AcOH (wherein AcO is the well-known designation for an acetoxy group, ($CH_3(CO)O$—)), or in chloroform, acetonitrile, or methanol.

Preferably, this embodiment is carried out by using N-chlorosuccinimide, Iodo-gen®, tBuOOH, AcOOH, or $H_2O_2$.

According to a preferred embodiment, this step is carried out for 5 minutes to 24 hours, and preferably for 2 hours.

According to a preferred embodiment, this step is carried out at a temperature of 20° C. to 150° C., and preferably at 100° C., in the presence of $Na^{125}I$.

According to a preferred embodiment, the present invention relates to the preparation of a compound of formula (III) wherein X is astatine, by halodestannylation and radioastatination of a compound of formula (II) as defined above. Such compounds of formula (III) are used then to prepare compounds of formula (I) as defined above wherein X is astatine.

This embodiment is preferably carried out in MeOH/AcOH, or in chloroform, acetonitrile, or methanol.

Preferably, this embodiment is carried out by using N-chlorosuccinimide, Iodo-gen®, tBuOOH, AcOOH, or $H_2O_2$.

According to a preferred embodiment, this step is carried out for 5 minutes to 120 minutes, and preferably for 30 minutes.

According to a preferred embodiment, this step is carried out at a temperature of 20° C. to 150° C., and preferably at 100° C.

The known oxidation methods already described in Amey R L, Martin J C (1979) *J. Org. Chem.* 44; 1779-1784 concerning compound 2:

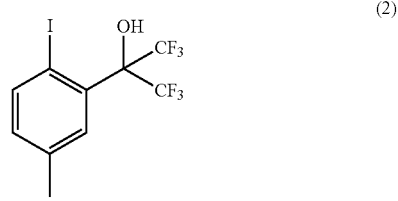 [SMILES: Cc1ccc(I)c(C(O)(C(F)(F)F)C(F)(F)F)c1]

have been adapted to make them suitable for radioactive conditions, i.e. fast reactions carried out in small volume (50 to 500 μL) as well as in very diluted solutions.

The hypervalent bond formation was first studied on non radioactive compound 2 prepared by a slightly modified method of the one described by Amey. Starting from para-toluidine, the introduction of perfluoroalkyl group was carried out with hexafluoroacetone sesquihydrate which is a liquid, instead of anhydrous hexafluoroacetone which is a gas. This method which is safer and easier to set up gave a compound with similar yield (76%). The iodination was carried out by formation of the aryldiazonium followed by nucleophilic substitution with potassium iodide. The suppression of the Copper-bronze catalyst lead to better yields than the original synthesis (71%).

Scheme 1 - Preparation of compounds 5a and 5b

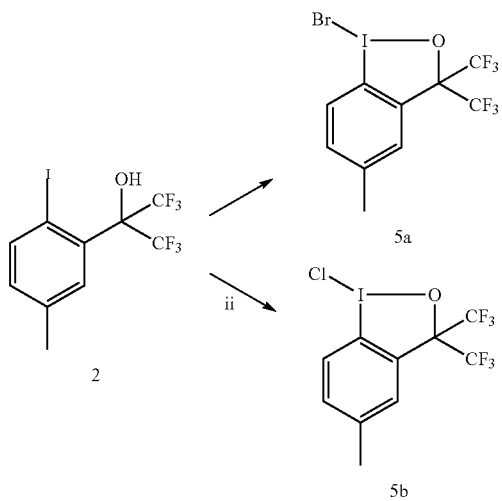

(i) propan-2-ol, NBS, 50° C., 30 min; (ii) propan-2-ol, NaOCl, HCl, rt, 5 min

To form bromoarylalkoxyiodinane 5a, the best conditions were the introduction of 1.05 eq of N-Bromosuccinimide on compound in iso-propanol and heating at 50° C. (i of Scheme 1). After 30 min, we observed the complete conversion into the desired hypervalent species. The chlorinated analogue 5b was obtained by generating chlorine in situ with sodium hypochlorite and hydrochloric acid (ii of Scheme 1). In iso-propanol, the chloroarylalkoxyiodinane is formed instantaneously at room temperature.

These conditions were used to prepare the radioiodinated analogues 7a (compound having formula (I-11)) and 7b (compound having formula (I-12)). Since iodine and astatine have similar chemical properties, results obtained with 5a and 5b could be used for reactivity and analytical comparisons with astatinated compounds. They were prepared by halodestannylation of compound 4 (compound having formula (I-3)). This tin precursor was obtained in two steps from compound 2 (scheme 2):

Scheme 2 - Preparation of compounds 2 and 4

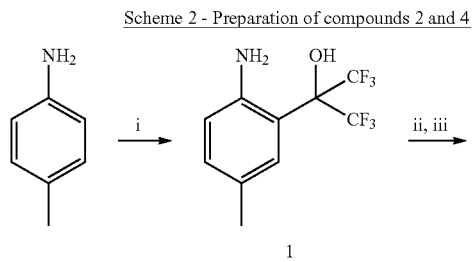

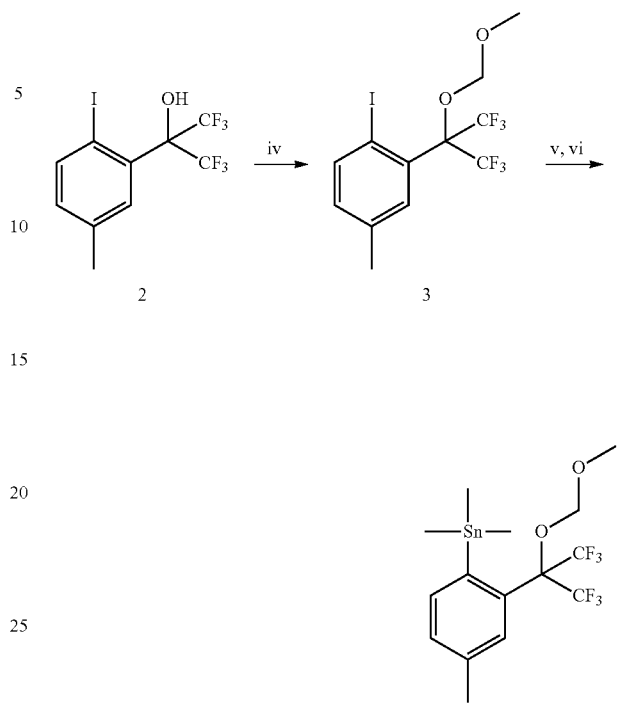

(i) chlorobenzene, $(CF_3)_2CO$. 1,5 $H_2O$, 100° C., 5 h; (ii) water, $NaNO_2$, $H_2SO_4$, 0° C., 30 min; (iii) KI, 80° C., 30 min; (iv) N,N-diisopropylethylamine, MOMCl, rt, overnight; (v) THF, n-BuLi, -78° C., 30 min; (vi) $Me_3SnCl$, -78° C. to rt It was first necessary to protect the hydroxyl group (iv of Scheme 2), otherwise it was not possible to introduce properly the tin group. The MOM protection seemed to be one of the best protecting groups for this purpose because it is not too bulky, allowing tin introduction. Furthermore, it is quickly removed under acidic conditions (which is of major importance for radiolabeling with a short-lived radioisotope as astatine-211). The trimethyltin group was introduced by n-butyl-lithium metallation (v of Scheme 2) followed by substitution with trimethyltin chloride (vi of Scheme 2). Deprotection of the hydroxyl was attempted before radiolabeling, but the acidic conditions required lead to simultaneous hydrolysis of the tin group.

The radioiodination was carried out using standard process (Scheme 3):

Scheme 3 - Preparation of radioactive arylalkoxyiodinanes synthesis

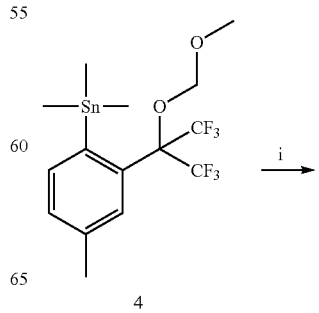

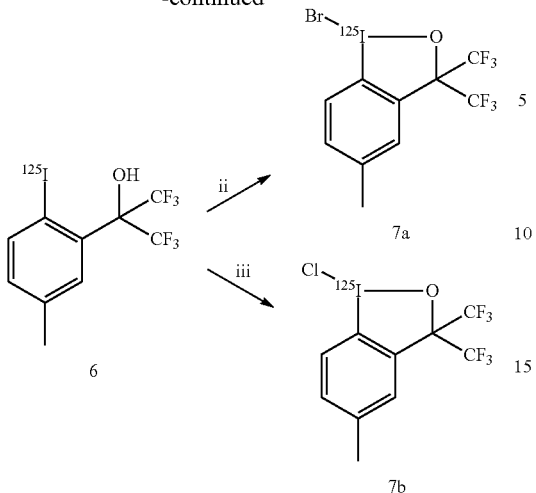

(i) MeOH/AcOH, Na$^{125}$I, NCS, 100° C., 2 h; (ii) propan-2-ol, NBS, 30 min, 60° C. (iii) HCl, NaOCl, 30 min, 60° C.

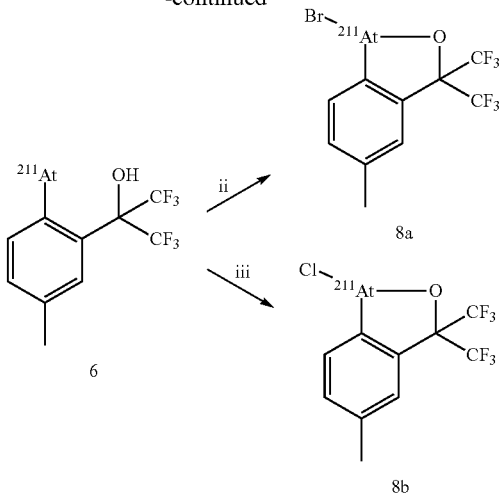

(i) MeOH/AcOH, $^{211}$At, NCS, 100° C., 30 min; (ii) propan-2-ol, NBS, 30 min, 60° C. (iii) HCl, NaOCl, 30 min, 60° C.

Briefly, to the tin precursor 4 was added 5 equivalents of N-chlorosuccinimide and 100 µCi 1-125 (I of Scheme 3). It was necessary to heat 30 nm at 100° C. to obtain a quantitative substitution. The reaction mixture was then composed of the labeled compound 6 and unprotected intermediate. The relatively slow deprotection rate of the MOM protection was due to the mildly acidic conditions of the mixture (5% acetic acid in methanol as solvent). It was necessary to maintain the temperature at 100° C. over 2 h to complete the deprotection. A slight difference was noticed in the astatination process. Using the same conditions, compound 6 was obtained quantitatively in 15 min at 100° C. then no deprotection step was necessary. This can be explained by the reactivity difference between iodine and astatine. While iodine cation can react on the intact tin precursor 2, the astatine cation which is to bulky needs the MOM group to be removed to access the reactive carbon.

The oxidation step gave the same results for iodine-125 and astatine-211 and the total conversion of the monovalent into the hypervalent radiohalogens could be achieved in 30 min at 60° C. using N-bromosuccinimide or NaOCl/HCl to form the brominated hypervalent species (7a and 7b) or the chlorinated hypervalent species (8a and 8b) respectively in quantitative yields.

Scheme 4 - Preparation of radioactive arylalkoxyastatinanes synthesis

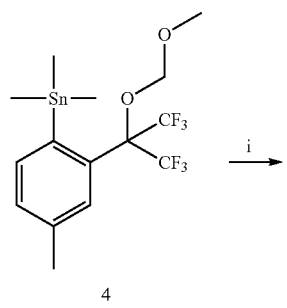

The stannic precursor (compound having formula (II)) was designed to increase the stability of the hypervalent bonds. The factors contributing to the stability are the inclusion of astatine in a five membered ring and the electronegativity of the apical oxygen strengthened by the presence of trifluoromethyl groups.

The present invention also relates to a pharmaceutical composition, comprising a compound having formula (I) as defined above, in association with at least one pharmaceutically acceptable excipient, said compound being if necessary coupled to a vector chosen from biomolecules and nanocarrrier compounds.

While it is possible for the compounds of the invention having formula (I) to be administered alone it is preferred to present them as pharmaceutical compositions. The pharmaceutical compositions, both for veterinary and for human use, useful according to the present invention comprise at least one compound having formula (I) as above defined, together with one or more pharmaceutically acceptable carriers and optionally other therapeutic ingredients.

In certain preferred embodiments, active ingredients necessary in combination therapy may be combined in a single pharmaceutical composition for simultaneous administration.

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The pharmaceutical compositions can be administered in a suitable formulation to humans and animals by topical or systemic administration, including oral, rectal, nasal, buccal, ocular, sublingual, transdermal, rectal, topical, vaginal, parenteral (including subcutaneous, intra-arterial, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The compounds having formula (I) as defined above may be used alone in pharmaceutical compositions or may be coupled to a vector before their administration. The term "vector" is defined above and refers in particular to a biomolecule such as antibodies or fragments thereof or any antibody construct (like minibodies, diabodies etc. . . . resulting of antibody engineering), peptides or haptens, or to a nanocarrier compound able to recognize the target cells such as a nanocapsule, a liposome, a dendrimer or a carbon nanotube. Said target cells are the cells in which the radionuclides have to be transported in order to kill or detect said cells.

The present invention also relates to a compound having formula (I) as defined above (administered alone or coupled to a vector), for its use for the treatment or detection of tumors. In particular, the present invention also relates to a compound having formula (I) as defined above wherein X is $^{211}$At (administered alone or coupled to a vector), for its use for the treatment or detection of small tumor burden, small disseminated tumors, myeloma or lymphoma.

As used herein, the term or "disseminated" refers to being scattered or distributed over a range (in area or volume), whether evenly or unevenly, such as being spread over a large area of a body, tissue, or organ.

According to an advantageous embodiment, the present invention relates to a compound having formula (I) as defined above wherein X is $^{123}$I or $^{124}$I (administered alone or coupled to a vector), for its use for the detection of tumors.

According to an advantageous embodiment, the present invention relates to a compound having formula (I) as defined above wherein X is $^{131}$I or $^{211}$At (administered alone or coupled to a vector), for its use for the treatment of tumors.

EXAMPLES

NMR spectra were recorded on a BRUKER AC 250 apparatus (250.133 MHz) for $^1$H and on a BRUCKER AC 400 (100,623 MHz) for $^{13}$C. Chemical shifts are indicated in δ values (ppm) and coupling constants (J) are given in Hertz (Hz). Multiplicities were recorded as s (singlet), d (doublet), t (triplet), septet or m (multiplet). Mass spectra were recorded using a Bruker Esquire LC electrospray mass spectrometer with acetonitrile as carrier solvent.

Chemicals were obtained from the Sigma-Aldrich company exept 1,1,1,3,3,3-hexafluoroacetone sesquihydrate, N,N-diisopropylethylamine and n-butyllithium solution from Acros organics. Solvents were obtained from Fisher Scientific except, diethylether, THF, acetic acid and carbon tetrachloride from Carlo Erba-SDS Reactions were followed by thin layer chromatography revealed by UV, iodine, ninhydrine (for compounds with amino group) or by phosphor-imaging detection for radioactive samples scanned with a typhoon scanner (Amersham Bioscience).

Astatine was produced at the Klinik für Nuklearmedizin's Hannover's cyclotron (MC35, Scanditronix) by the $^{209}$Bi(α, 2n)$^{211}$At reaction, and dry distilled from the target. The activity was recovered in methanol.

Sodium [$^{125}$I] iodide was obtained from Perkin Elmer (Boston, Mass., USA).

Example 1

Preparation of Compound 4 Having Formula (I-3)

1. Preparation of Compound 1 (See Above Scheme 1)

2-(2-amino-5-methylphenyl)-1,1,1,3,3,3-hexafluoropropan-2-ol (1)

To a solution of para-toluidine (14.6 g, 136 mmol) in chlorobenzene (25 mL) was added paratoluenesulphonic acid monohydrate (395 mg, 2.05 mmol). The reaction mixture was heated at 100° C. and 1,1,1,3,3,3-hexafluoroacetone sesquihydrate (41.4 g, 219 mmol) was added drop-wise over 45 min through a dropping funnel. The mixture was stirred for 5 h at 100° C. After solvent removal, the residue was dissolved in chloroform (300 mL) and placed overnight at −20° C. The crystals formed were filtered and washed with cooled chloroform to give 28.2 g of white needles (103.4 mmol, 76% yield) after drying overnight under vacuum.

$^1$H(CDCl$_3$) δ 2.36 (s, 3H), 6.97 (d, 1H, J=7.93 Hz), 7.18 (d, 1H, J=7.93 Hz), 7.39 (s, 1H).

$^{13}$C(CDCl$_3$) δ 21.0 (s), 79.9 (septet, 2JC-F=30 Hz), 122.8 (s), 123.4 (q, 1JC-F=286 Hz), 127.2 (s), 128.9 (septet, 3JC-F=2 Hz), 131.1 (s), 135.1 (s), 138.6 (s).

MS (ES+) m/z 274.0 [M+H]+, 256.0 [M+H—H$_2$O]+.

mp: 110° C.

2. Preparation of Compound 2 (See Above Scheme 1)

1,1,1,3,3,3-hexafluoro-2-(2-iodo-5-methylphenyl)propan-2-ol (2)

To compound 1 (2 g, 7.32 mmol) in suspension in distilled water (20 mL) cooled in a ice-bath was added sulfuric acid (0.5 mL). Sodium nitrite (505 mg, 7.32 mmol) dissolved in water (2.5 mL) was added dropwise and another 0.5 mL sulfuric acid was added. The mixture was stirred at 0° C. until complete dissolution of the suspension (ca 30 min). The solution was added dropwise over 30 min to ice cooled potassium iodide (1.46 g, 8.78 mmol) dissolved in distilled water (5 mL). The reaction mixture when then heated at 80° C. until nitrogen formation stops (ca 30 min). After return to room temperature, the red suspension was filtered, washed with water and dissolved in diethylether (50 mL). It was washed with water (20 mL) and 1N hydrochloric acid (20 mL). The organic layer was dried over sodium sulfate and concentrated under vacuum. The residue was chromatographied on a silica gel column with heptane/chloroform (1/1) as eluent to give 1.98 g (5.16 mmol, 71% yield) of a yellow oil which solidifies at 4° C. over night.

$^1$H (CDCl$_3$) δ 2.35 (s, 3H), 6.93 (d, 1H, J=8.24 Hz), 7.42 (s, 1H), 7.98 (d, 1H, J=8.24 Hz).

$^{13}$C (CDCl$_3$) δ 21.1 (s), 78.7 (septet, 2JC-F=30 Hz), 86.4 (s), 122.6 (q, 1JC-F=289 Hz), 129.5 (s), 130.7 (s), 132.5 (s), 138.3 (s), 144.3 (s).

MS (ES−) m/z 382.8 [M−H]−.

mp: 38-39° C.

3. Preparation of Compound 3 (See Above Scheme 1)

2-(1,1,1,3,3,3-hexafluoro-2-(methoxymethoxy)propan-2-yl)-1-iodo-4-methylbenzene (3)

Compound 2 (4 g, 10.42 mmol) was dissolved in N,N-diisopropylethylamine (DIPEA, 20 mL) freshly distilled over calcium hydride. The solution was cooled in an ice-bath and the chloromethyl methyl ether (4.75 mL, 62.5 mmol) was added. A white precipitate appeared instantaneously. The reaction mixture was stirred overnight at room temperature. After removal of DIPEA under vacuum, the residue was chromatographied over silica gel using heptane/acetone (97/3) to give 4.23 g (9.89 mmol, 95% yield) of a slightly yellow solid.

$^1$H (CDCl$_3$) δ 2.35 (s, 3H), 3.56 (s, 3H), 5.03 (s, 2H), 6.92 (d, 1H, J=7.93 Hz), 7.40 (s, 1H), 8.07 (d, 1H, J=7.93 Hz).

$^{13}$C (CDCl$_3$) δ 21.2 (s), 57.1 (s), 83.5 (septet, 2JC-F=29 Hz), 88.7 (s), 95.0 (s), 122.6 (q, 1JC-F=291 Hz), 126.9 (s), 129.5 (s), 132.4 (s), 132.5 (s), 138.3 (s), 145.0 (s).

mp: 41° C.

4. Preparation of Compound 4 (See Above Scheme 1)

(2-(1,1,1,3,3,3-hexafluoro-2-(methoxymethoxy)propan-2-yl)-4-methylphenyl)trimethylstannane (4)

Compound 3 (2.044 g, 4.77 mmol) was dissolved in freshly distilled THF (35 mL) under nitrogen.

The mixture was cooled to −78° C. with a acetone/dry-ice bath and 1.6M n-BuLi in hexane was added (4.45 mL, 7.16 mmol). The mixture was stirred 30 min at −78° C. and trimethyltin chloride (1.427 g, 7.16 mmol) in solution in THF (15 mL) was added. The reaction mixture was left to warm to room temperature over 3 h. The THF was removed under vacuum and the residue was chromatographied over silica gel using heptane/dichloromethane (95/5) to give 879 mg (1.89 mmol, 40% yield) of a white solid.

$^1$H (CDCl$_3$) δ 0.31 (s, 9H), 2.38 (s, 3H), 3.52 (s, 3H), 5.00 (s, 2H), 7.24 (d, 1H, J=7.6 Hz), 7.45 (s, 1H), 7.54 (d, 1H, J=7.6 Hz).

$^{13}$C (CDCl$_3$) δ −5.1 (s), 21.4 (s), 57.4 (s), 94.9 (s), 122.8 (q, 1JC-F=288 Hz), 129.2 (s), 130.1 (s), 134.1 (s), 137.7 (s) 137.9 (s), 140.8 (s).

mp: 38° C.

Example 2

Preparation of Compound 5a

1-Bromo-1,3-dihydro-5-methyl-3,3-bis(trifluoromethyl)-1,2-benziodoxole

Compound 2 (100 mg, 0.26 mmol) was dissolved in 5 mL propan-2-ol and N-bromosuccinimide (48.7 mg, 0.273 mmol) is added. The reaction mixture was heated 30 min at 50° C. After removal of the solvent under vacuum, the residue was purified over silica gel column using dichloromethane as eluant to give 111 mg (0.26 mmol, 92% yield) of a yellow solid.

$^1$H (CDCl$_3$) δ 2.56 (s, 3H), 7.47 (s, 1H), 7.61 (d, 1H, J=8.6 Hz), 7.87 (d, 1H, J=8.6 Hz).

$^{13}$C (CDCl$_3$) δ 20.9 (s), 84 (m), 106.3 (s), 122.8 (d, 1JC-F=288 Hz), 129.5 (s), 130.2 (s), 132.4 (s), 132.5 (s), 134.6 (s), 142.9 (s).

MS (ES−) m/z 460.4/462.4 [M−H]−, 382.3 [M−Br]−.

mp: 189-190° C.

Example 3

Preparation of Compound 5b 1-chloro-1,3-dihydro-5-methyl-3,3-bis(trifluoromethyl)-1,2-benziodoxole Compound 2 (60 mg, 156 μmol) was dissolved in 2 mL propan-2-ol, 10 μL hydrochloric acid (37%) and 50 μL sodium hypochlorite solution (10-15% in water) were added. A white precipitate appeared instantaneously. The reaction mixture was stirred 5 min at room temperature. The solvent was removed under vacuum and the residue was purified over silica gel column using dichloromethane as eluant to give 50 mg (119 μmol, 76% yield) of a white solid.

1H (CDCl$_3$) δ 2.56 (s, 3H), 7.51 (s, 1H), 7.64 (d, 1H, J=8.85 Hz), 7.92 (d, 1H, J=8.85 Hz).

MS (ES+) m/z 384.8 [M+H]+.

mp: 181-182° C.

Example 4

Preparation of Compound Having Formula (I-11)

[$^{125}$I]-1-Bromo-1,3-dihydro-5-methyl-3,3-bis(trifluoromethyl)-1,2-benziodoxole (7a).

Compound 4 (237 nmol in 100 μL MeOH/AcOH 95/5), N-chlorosuccinimide (2.02 μmol in 100 μL MeOH/AcOH 95/5) and sodium [$^{125}$I] iodide (3.7 MBq in 1 μL NaOH 0.048N) were heated 2 h at 100° C. To 100 μL of the reaction mixture were added N-bromosuccinimide (847 μmol in 100 μL propan-2-ol). After heating 30 min at 50° C., a TLC plate using heptane/acetone (3/2) as eluant showed a quantitative radiochemical yield.

Example 5

Preparation of Compound Having Formula (I-12)

[$^{125}$I]-1-chloro-1,3-dihydro-5-methyl-3,3-bis(trifluoromethyl)-1,2-benziodoxole (7b)

Compound 4 (237 nmol in 100 μL MeOH/AcOH 95/5), N-chlorosuccinimide (2.02 μmol in 100 μL MeOH/AcOH 95/5) and sodium [125I] iodide (3.7 MBq in 1 μL NaOH 0.048N) were heated 2 h at 100° C. To 25 μL of the reaction mixture were added 2 μL 37% hydrochloric acid and 2 μL 10-15% sodium hypochlorite. After heating 30 min at 50° C., a TLC plate using heptane/acetone (3/2) as eluant showed a quantitative radiochemical yield.

Example 6

Preparation of Compound Having Formula (I-9)

[$^{211}$At]-1-Bromo-1,3-dihydro-5-methyl-3,3-bis(trifluoromethyl)-1,2-benzastatoxole (8a)

Compound 4 (10 nmol in 4 μL MeOH/AcOH 95/5), N-chlorosuccinimide (60 nmol in 3 μL MeOH/AcOH 95/5) and the astatine-211 activity (0.5 to 5 MBq in 50 μL MeOH) were heated 30 min at 100° C. To 25 μL of the reaction mixture were added N-bromosuccinimide (212 μmol in 25 μL propan-2-ol). After heating 30 min at 50° C., a TLC plate using heptane/acetone (3/2) as eluant showed a quantitative radiochemical yield.

Example 7

Preparation of Compound Having Formula (I-10)

[$^{211}$At]-1-chloro-1,3-dihydro-5-methyl-3,3-bis(trifluoromethyl)-1,2-benzastatoxole (8b)

Compound 4 (10 nmol in 4 μL MeOH/AcOH 95/5), N-chlorosuccinimide (60 nmol in 3 μL MeOH/AcOH 95/5) and s the astatine-211 activity (0.5 to 5 MBq in 50 μL MeOH) were heated 30 min at 100° C. To 25 μL of the reaction mixture were added 2 μL 37% hydrochloric acid and 2 μL 10-15% sodium hypochlorite. After heating 30 min at 50° C., a TLC plate using heptane/acetone (3/2) as eluant showed a quantitative radiochemical yield.

Example 8

Preparation of Intermediate Compound Having Formula (I-4)

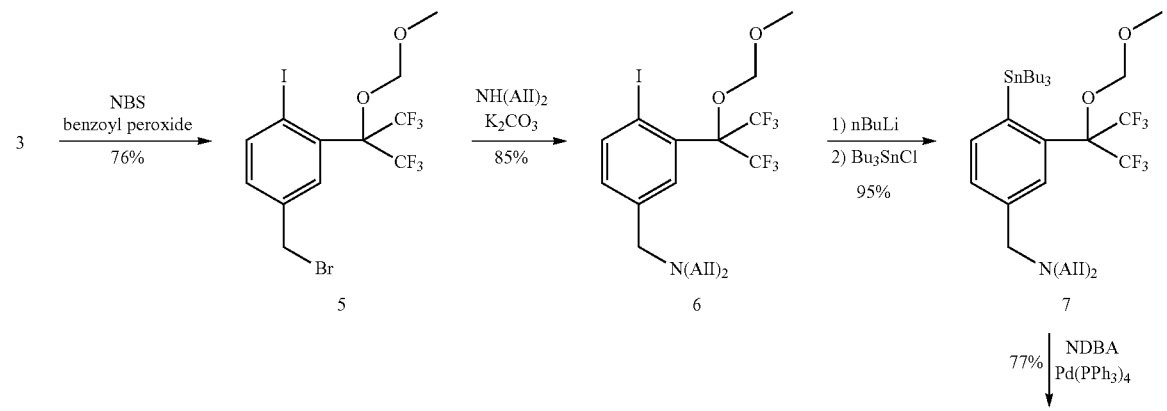

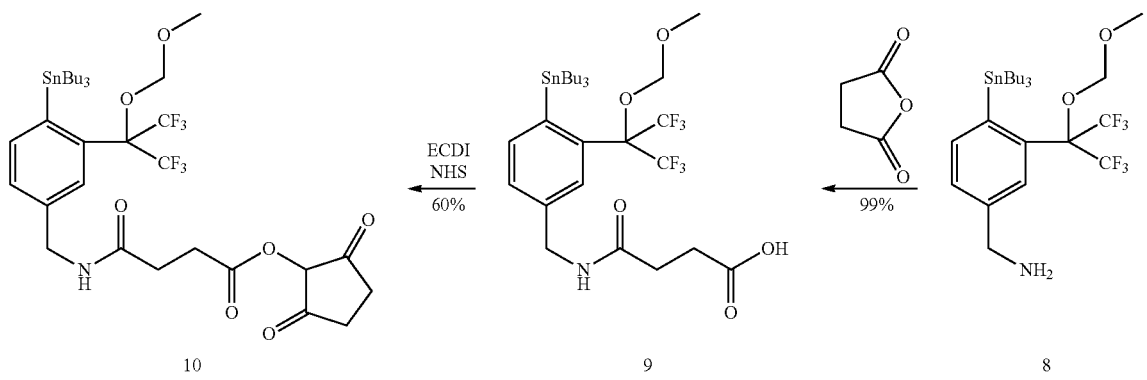

1. Preparation of Compound 5 (See Above Scheme)

4-(bromomethyl)-2-(1,1,1,3,3,3-hexafluoro-2-(methoxymethoxy)propan-2-yl)-1-iodobenzene (5)

Compound 3 (2.51 g, 5.86 mmol), benzoyl peroxide (57 mg, 256 µmol) and N-bromosuccinimide (1.038 g, 8.79 mmol) were dissolved in 25 mL carbon tetrachloride. The solution was degassed, placed under nitrogen atmosphere and heated 15 h at 78° C. After cooling to room temperature, the mixture was filtered, and the solid washed with carbon tetrachloride. The filtrate was evaporated under reduced pressure to give a residue which was purified over silica gel using heptane/acetone as eluant to give 2.27 g (4.48 mmol, 76% yield) of a white solid.

$^1$H (CDCl$_3$) δ 3.57 (s, 1H), 4.43 (s, 2H), 5.03 (s, 2H), 7.15 (d, 1H, J=8.2 Hz), 7.58 (s, 1H), 8.18 (d, 1H, J=8.2 Hz).
mp: 93° C.

2. Preparation of Compound 6 (See Above Scheme)

N-allyl-N-(3-(1,1,1,3,3,3-hexafluoro-2-(methoxymethoxy)propan-2-yl)-4-iodobenzyl)prop-2-en-1-amine (6)

Compound 5 (1.07 g, 2.11 mmol) was dissolved in anhydrous acetonitrile (20 mL) under nitrogen atmosphere. Potassium carbonate (583 mg, 4.22 mmol), potassium iodide (350 mg, 2.11 mmol) and diallylamine (2.6 mL, 21.1 mmol) were added and the reaction mixture heated at 80° C. overnight. After cooling to room temperature, the salts were filtered and the filtrate ware evaporated under reduced pressure. The residue was purified over silica gel using heptane/acetone (9/1) as eluant to give 936 mg (1.79 mmol, 85% yield) of a yellowish oil.

$^1$H (CDCl$_3$) δ 3.07 (d, 4H, J=6.4 Hz), 3.57 (s, 5H), 5.03 (s, 2H), 5.13-5.22 (m, 4H), 5.76-5.92 (m, 2H), 7.07 (d, 1H, J=8.2 Hz), 7.65 (s, 1H), 8.12 (d, 1H, 8.2 Hz).
MS (ES+) m/z 524.0 [M+H]+.

3. Preparation of Compound 7 (See Above Scheme)

N-allyl-N-(3-(1,1,1,3,3,3-hexafluoro-2-(methoxymethoxy)propan-2-yl)-4-(tri butylstannyl)benzyl)prop-2-en-1-amine (7)

Compound 7 (533 mg, 1.02 mmol) was dissolved in freshly distilled THF (5 mL) under nitrogen atmosphere and cooled to −78° C. n-butyllithium 1.6M in hexane solution (955 µL, 1.53 mmol) was then added and the mixture stirred 30 min at −78° C. Tributyltin chloride (497 mg, 1.53 mmol) in solution in THF (3 mL) was added and the mixture let to warm to room temperature overnight. A 0.1M ammonium chloride solution (5 mL) was added to the reaction mixture. The organic layer was isolated and the aqueous layer was extracted with dichloromethane (2×5 mL). The organic layers were combined and dried over sodium sulfate. After solvent evaporation under reduced pressure, the residue was purified over silica gel with heptane/acetone (98/2) as eluant to give 662 mg (0.96 mmol, 95% yield) of a colorless oil.

$^1$H (CDCl$_3$) δ 0.89 (t, 9H, J=7.0 Hz), 1.08 (t, 6H, J=8.3 Hz), 1.28-1.47 (m, 12H), 3.08 (d, 4H, J=6.1 Hz), 3.52 (s, 3H), 3.6 (s, 2H), 4.89 (s, 2H), 5.13-5.23 (m, 4H), 5.78-5.95 (m, 2H), 7.35 (d, 1H, 7.6 Hz), 7.54 (d, 1H, J=7.6 Hz), 7.63 (s, 1H).
MS (ES+) m/z 688.2 [M+H]+, 398.2 [M+2H—SnBu$_3$]+.

4. Preparation of Compound 8 (See Above Scheme)

(3-(1,1,1,3,3,3-hexafluoro-2-(methoxymethoxy)propan-2-yl)-4-(tributylstannyl)phenyl)methanamine (8)

Compound 7 (622 mg, 906 µmol) was dissolved in dichloromethane (10 mL) and the solution was degassed by nitrogen bubbling over 15 min. The solution was then added to N,N-dimethylbarbituric acid (849 mg, 5.44 mmol) and Tetrakis (triphenylphosphine)palladium(0) (21 mg 18.1 µmol) placed in a two necked flask under nitrogen atmosphere and the resulting mixture was warmed 4 h at 35° C. The solvent was removed under vacuum, the residue dissolved in diethylether (20 mL), and washed with a 0.1M sodium carbonate solution (3×10 mL). The organic layer was dried over sodium sulfate and concentrated under vacuum. The residue was purified over silica gel using dichloromethane/methanol (95/5) to give 423 mg (698 µmol, 77% yield) of a yellowish oil.

$^1$H (CDCl$_3$) δ 0.89 (t 9H, J=7.0 Hz), 1.08 (t, 6H, J=8.3 Hz), 1.28-1.50 (m, 12H), 1.98 (s, 2H), 3.52 (s, 3H), 3.91 (s, 2H), 4.88 (s, 2H), 7.38 (d, 1H, J=6.7 Hz), 7.56-7.60 (m, 2H).
$^{13}$C (CDCl$_3$) δ 12.9, 13.6, 27.4, 29.0, 57.2, 83.0 (m), 122.7 (q, $^1J_{C-F}$=290 Hz), 127.9, 128.1, 134.7, 138.8, 144.2.
MS (ES+) m/z 608.1 [M+H]+.

5. Preparation of Compound 9 (See Above Scheme)

4-(3-(1,1,1,3,3,3-hexafluoro-2-(methoxymethoxy)propan-2-yl)-4-(tributylstannyl)benzylamino)-4-oxobutanoic acid (9)

Compound 8 (401 mg, 661 µmol) was dissolved in freshly distilled THF (5 mL) under nitrogen atmosphere and succinic anhydride (165 mg, 1.65 mmol) was added. After stirring 20 h at 20° C., the solvent was removed under reduced pressure and dissolved in n-hexane. The white precipitate was removed by filtration and the filtrate evaporated to dryness. The residue was purified over silica gel by dichloromethane/methanol (9/1) to give 461 mg (661 µmol, 99% yield) of a white solid.

$^1$H (CDCl$_3$) δ 0.89 (t, 9H, J=7.0 Hz), 1.09 (t, 6H, J=8.2 Hz), 1.28-1.50 (m, 12H), 2.57 (t, 2H, J=7.0 Hz), 2.76 (t, 2H, J=7.0 Hz), 3.52 (s, 3H), 4.48 (d, 2H, J=5.8 Hz), 4.88 (s, 2H), 6.07 (t, 1H, J=5.8 Hz), 7.32 (d, 1H, J=7.6 Hz), 7.49 (s, 1H), 7.59 (d, 1H, J=7.6 Hz).
MS (ES+) m/z 708.1 [M+H]+, 730.1 [M+Na]+, 746.1 [M+K]+.

6. Preparation of Compound 10 (See Above Scheme)

2,5-dioxopyrrolidin-1-yl 4-(3-(1,1,1,3,3,3-hexafluoro-2-(methoxymethoxy) propan-2-yl)-4-(tri butylstannyl)benzylamino)-4-oxobutanoate (10)

Compound 9 (66 mg, 93 µmol) was dissolved in acetonitrile (2 mL), N-hydroxysuccinimide (21.5 mg, 187 µmol) and EDCI (36 mg, 187 µmol) were added and the mixture stirred at 20° C. overnight. The solvent was removed under vacuum and the residue was purified over silica gel using dichloromethane/AcOEt (4/1) as eluant to give 45 mg (93 µmol, 60% yield) of a colorless oil.

$^1$H (CDCl$_3$) δ 0.88 (t, 9H, J=7.0 Hz), 1.07 (t, 6H, J=8.3 Hz), 1.23-1.49 (m, 12H), 2.66 (t, 2H, J=7.0 Hz), 2.73 (s, 4H), 3.03 (t, 2H, J=7.0 Hz), 3.51 (s, 3H), 4.47 (d, 2H, J=5.8 Hz), 4.87 (s, 2H), 6.02 (t, 1H, J=5.8 Hz), 7.31 (d, 1H, J=7.6 Hz), 7.48 (s, 1H), 7.58 (s, 1H, J=7.6 Hz).
MS (ES+) m/z 827.2 [M+Na]+, 1629.2 [2M+Na]+

Example 9

Preparation of Intermediate Compound Having Formula (II-5)

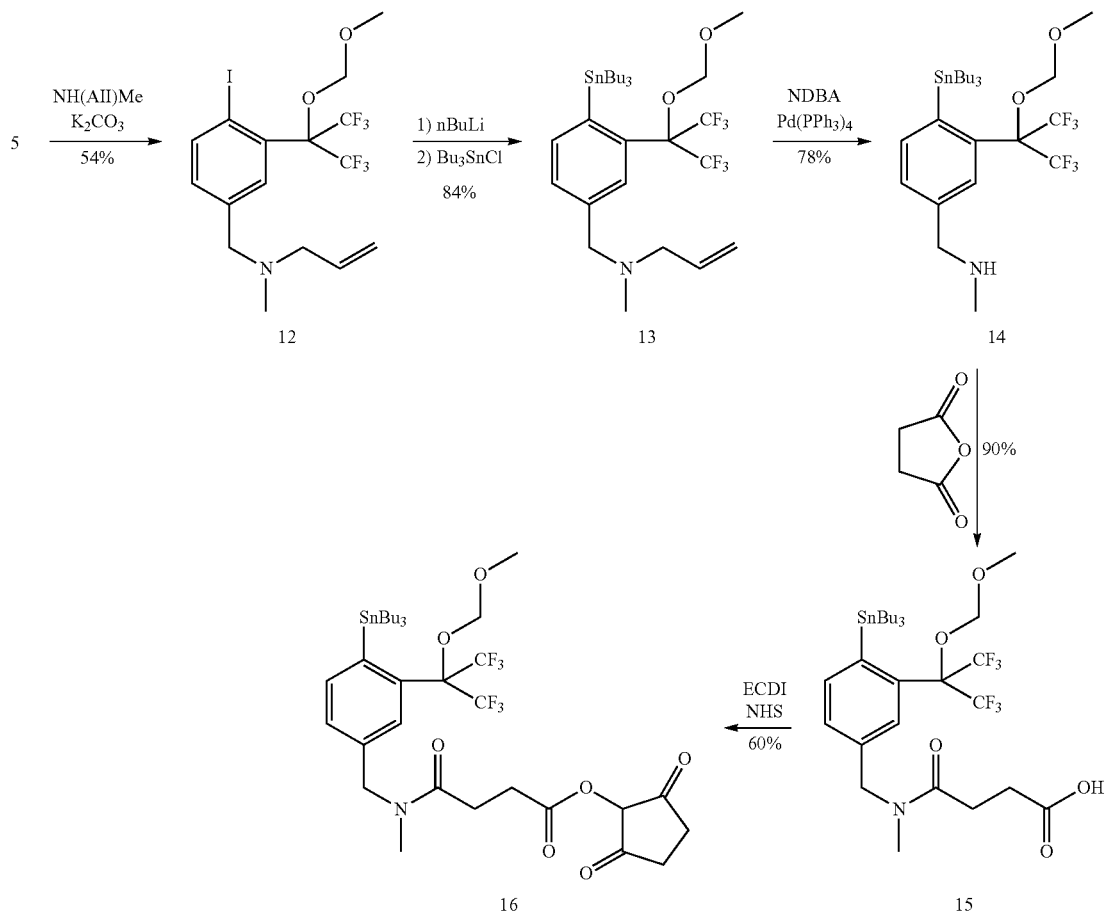

1. Preparation of Compound 12 (See Above Scheme)

N-(3-(1,1,1,3,3,3-hexafluoro-2-(methoxymethoxy)propan-2-yl)-4-iodo-benzyl)-N-methylprop-2-en-1-amine (12)

Compound 5 (500 mg, 986 µmol), was dissolved in anhydrous acetonitrile (5 mL) under nitrogen. Potassium carbonate (273 mg, 1.97 mmol), potassium iodide (164 mg, 986 µmol) and N-allylmethylamine (188 µL, 1.97 mmol) were added and the mixture heated at 40° C. overnight. After cooling to room temperature, the solvent was removed under reduced pressure and the residue chromatographied over silica gel using chloroform as eluant to give 265 mg (490 µmol, 54% yield) of a colorless oil.

$^1$H (CDCl$_3$) δ 2.20 (s, 3H), 3.02 (d, 2H, J=6.4 Hz), 3.50 (s, 2H), 3.57 (s, 3H), 5.03 (s, 2H), 5.15-5.24 (m, 2H), 5.79-5.24 (m, 1H), 7.09 (d, 1H, J=8.0 Hz), 7.58 (s, 1H), 8.14 (d, 1H, J=8.0 Hz).

MS (ES+) m/z 497.9 [M+H]$^+$

2. Preparation of Compound 13

N-(3-(1,1,1,3,3,3-hexafluoro-2-(methoxymethoxy)propan-2-yl)-4-(tributyl-stannyl)benzyl)-N-methyl-prop-2-en-1-amine (13)

Compound 12 (470 mg, 945 µmol) was dissolved in freshly distilled THF (5 mL) under nitrogen atmosphere and cooled to −78° C. n-butyllithium 1.6M in hexane solution (886 µL, 1.42 mmol) was then added and the mixture stirred 30 min at −78° C. Tributyltin chloride (462 mg, 1.42 mmol) in solution in THF (2 mL) was added and the mixture let to warm to room temperature overnight. A 0.1M ammonium chloride solution (5 mL) was added to the reactionnal mixture. The organic layer was isolated and the aqueous layer was extracted with dichloromethane (2×5 mL). The organic layers were combined and dried over sodium sulfate. After solvent evaporation under reduced pressure, the residue was purified over silica gel with heptane/acetone (98/2) as eluant to give 524 mg (794 µmol, 84% yield) of a yellowish oil.

$^1$H (CDCl$_3$) δ 0.89 (t, 9H, J=7.0 Hz), 1.08 (t, 6H, J=8.3 Hz), 1.28-1.47 (m, 12H), 2.22 (s, 3H), 3.04 (d, 2H, J=6.4 Hz), 3.52 (s, 3H), 3.54, (s, 2H), 4.89 (s, 2H), 5.16-5.25 (m, 2H), 5.83-5.97 (m, 1H), 7.38 (d, 1H, J=7.0 Hz), 7.55-7.58 (m, 2H).

MS (ES+) m/z 662.3 [M+H]$^+$

3. Preparation of Compound 14

(3-(1,1,1,3,3,3-hexafluoro-2-(methoxymethoxy)propan-2-yl)-4-(tributyl-stannyl)phenyl)-N-methyl-methanamine (14)

Compound 13 (270 mg, 409 μmol) was dissolved in dichloromethane (5 mL) and the solution was degassed by nitrogen bubbling over 15 min. The solution was then added to N,N-dimethylbarbituric acid (191 mg, 1.23 mmol) and Tetrakis (triphenylphosphine)palladium(0) (19 mg 16.4 μmol) placed in a two necked flask under nitrogen atmosphere and the resulting mixture was warmed 4 h at 35° C. The solvent was removed under vacuum, the residue dissolved in diethylether (10 mL), and washed with a 0.1M sodium carbonate solution (2×5 mL). The organic layer was dried over sodium sulfate and concentrated under vacuum. The residue was purified over silica gel using chloroform/methanol (9/1) to give 199 mg (321 μmol, 78% yield) of a yellowish oil.

$^1$H (CDCl$_3$) δ 0.89 (t, 9H, J=7.0 Hz), 1.08 (t, 6H, J=8.3 Hz), 1.28-1.47 (m, 12H), 2.46 (s, 3H), 3.52 (s, 3H), 3.78 (s, 2H), 4.88 (s, 2H), 7.38 (d, 1H, J=7.3 Hz), 7.55-7.59 (m, 2H).

$^{13}$C (CDCl$_3$) δ 12.9, 13.6, 27.4, 29.0, 33.9, 54.0, 57.3, 94.5, 129.2, 129.3, 134.7, 139.0.

MS (ES+) m/z 622.2 [M+H]$^+$.

4. Preparation of Compound 15

4-((3-(1,1,1,3,3,3-hexafluoro-2-(methoxymethoxy)propan-2-yl)-4-(tri butyl-stannyl)benzyl)(methyl)amino)-4-oxobutanoic acid (15)

Compound 14 (114 mg, 184 μmol) was dissolved in freshly distilled THF (3 mL) under nitrogen atmosphere and succinic anhydride (37 mg, 368 μmol) was added. After overnight at 20° C., the solvent was removed under reduced pressure and dissolved in n-hexane. The white precipitate was removed by filtration and the filtrate evaporated to dryness. The residue was purified over silica gel by dichloromethane/methanol (95/5) to give 119 mg (165 μmol, 90% yield) of a colorless oil.

$^1$H (CDCl$_3$) δ 0.89 (t, 9H, J=7.2 Hz), 1.08 (t, 6H, J=8.3 Hz), 1.30-1.47 (m, 12H), 2.68-2.77 (m, 4H), 2.97 (s, 1.86H), 2.98 (s, 1.14H), 3.51 (s, 1.86H), 3.52 (s, 1.14H), 4.58 (s, 0.76H), 4.62 (s, 1.24H), 4.89 (s, 1.24H), 4.92 (s, 0.76H), 7.21 (d, 0.38H, J=7.6 Hz), 7.26 (d, 0.62H, J=7.6 Hz), 7.39 (s, 0.38H), 7.43 (s, 0.62H), 7.58 (d, 0.62, J=7.6 Hz), 7.64 (d, 0.38H, J=7.6 Hz).

MS (ES+) m/z 744.2 [M+Na]$^+$, (ES−) m/z 719.8 [M−H]$^−$.

5. Preparation of Compound 16

2,5-dioxopyrrolidin-1-yl 4-((3-(1,1,1,3,3,3-hexafluoro-2-(methoxymethoxy) propan-2-yl)-4-(tributylstannyl)benzyl)(methyl)amino)-4-oxobutanoate (16)

Compound 15 (170 mg, 236 mmol) was dissolved in acetonitrile (5 mL), N-hydroxysuccinimide (54 mg, 472 mmol) and EDCI (90 mg, 472 μmol) were added and the mixture stirred 6 h at 20° C. The solvent was removed under vacuum and the residue was purified over silica gel using dichloromethane/acetone (1/1) as eluant to give 155 mg (190 μmol, 80% yield) of a colorless oil.

$^1$H (CDCl$_3$) δ 0.89 (t, 9H, J=7.2 Hz), 1.08 (t, 6H, J=8.3 Hz), 1.31-1.45 (m, 12H), 2.79-2.85 (m, 7H), 2.94+2.97 (2s, 1.86+1.14H), 3.02-3.08 (m, 2H), 3.51+3.52 (2s, 1.86+1.14H), 4.56+4.62 (2s, 0.76+1.24H), 4.89+4.91 (2s, 1.24+0.76H), 7.20+7.25 (2d, 0.38+0.62H, J=7.6 Hz), 7.39+7.42 (2d, 0.38+0.62H), 7.57+7.63 (2d, 0.62+0.38H, J=7.6 Hz).

$^{13}$C (CDCl$_3$) δ 12.8, 13.6, 25.3, 27.4, 29.0, 34.7, 50.9, 57.2, 94.4, 126.7, 128.4, 136.5, 138.7, 142.4, 168.5, 169.0, 170.3

MS (ES+) m/z 819.2 [M+H]$^+$, 841.3 [M+Na]$^+$, 857.3 [M+K]$^+$, 1655.4 [2M+Na]$^+$.

Example 10

Preparation of Intermediate Compound Having Formula (II-6)

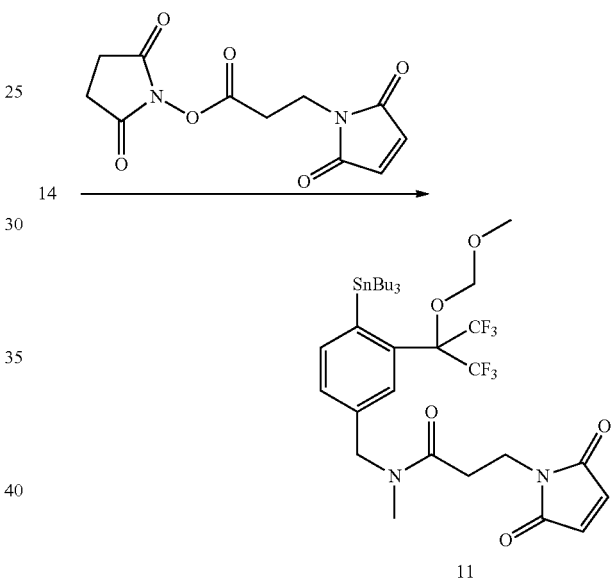

3-(2,5-dioxo-2H-pyrrol-1(5H)-yl)-N-(3-(1,1,1,3,3,3-hexafluoro-2-(methoxy-methoxy)propan-2-yl)-4-(tributylstannyl)benzyl)-N-methylpropanamide (11)

Compound 14 (86 mg, 138 μmol) was dissolved in anhydrous acetonitrile (2 mL) and 3-(Maleimido)propionic acid N-hydroxysuccinimide ester (44 mg, 166 mmol) was added. The mixture was stirred overnight at room temperature, the solvent removed under reduced pressure and the residue purified over silica gel using chloroform/methanol (98/2) as eluant to give 86 mg (111 μmol, 81% yield) of a colorless oil.

$^1$H (CDCl$_3$) δ 0.89 (t, 9H, J=7.3 Hz), 1.08 (t, 6H, J=78.5 Hz), 1.30-1.48 (m, 12H), 2.68-2.75 (m, 2H), 2.83 (s, 1.95H), 2.90 (s, 1.05H), 3.52 (s, 3H), 3.87-3.96 (m, 2H), 4.51 (s, 0.7H), 4.58 (s, 1.3H), 6.68-6.74 (m, 2H), 7.18 (d, 0.35H, J=7.6 Hz), 7.27 (d, 0.65H, J=7.6 Hz), 7.37 (s, 0.35H), 7.42 (s, J=0.65H), 7.55 (d, 0.35H, J=7.6 Hz), 7.62 (d, 0.65H, J=7.6 Hz).

MS (ES+) m/z 773.4 [M+H]$^+$, 795.4 [M+Na]$^+$.

Example 11

Preparation of Intermediate Compound Having Formula (II-7)

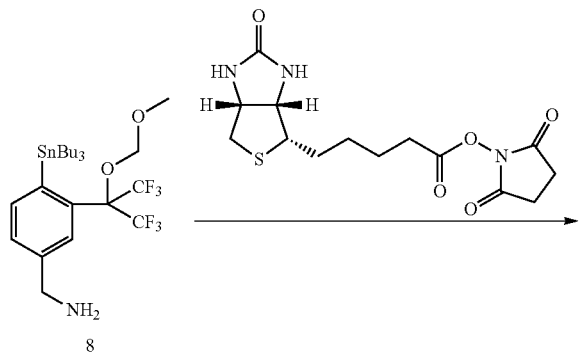

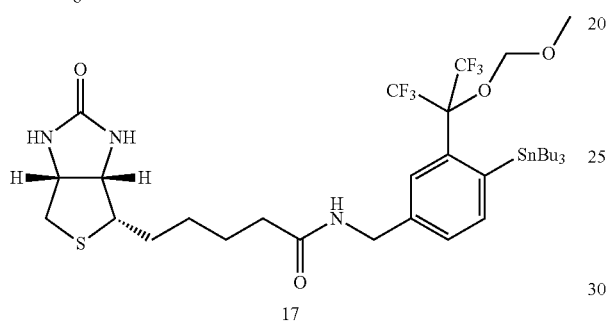

N-(3-(1,1,1,3,3,3-hexafluoro-2-(methoxymethoxy)propan-2-yl)-4-(tri butyl-stannyl)benzyl)biotinamide (17)

Compound 8 (111 mg, 183 µmol) was dissolved in anhydrous DMF (2 mL) under nitrogen atmosphere, and biotin N-hydroxysuccinimidyl ester (66 mg, 192 µmol) was added. The mixture was stirred overnight at 20° C., the solvent removed under reduced pressure and the residue purified over silica gel using dichloromethane/methanol (95/5) as eluant to give 97 mg (117 µmol, 64% yield) of a colorless oil.

$^1$H (CDCl$_3$) δ 0.89 (t, 9H, J=7.0 Hz), 1.07 (t, 6H, J=8.3 Hz), 1.27-1.48 (m, 12H), 1.70 (m, 6H), 2.27 (t, 2H, J=7.3 Hz), 2.67 (d, 1H, J=12.5 Hz), 2.85-2.92 (m, 1H), 3.10-3.17 (m, 1H), 3.51 (s, 3H), 4.26-4.31 (m, 1H), 4.45-4.47 (m, 2H), 4.86 (s, 2H), 5.08 (s, 1H), 6.28-6.32 (m, 1H), 7.31 (d, 1H, J=7.6 Hz), 7.48 (s, 1H), 7.58 (d, 1H, J=7.6 Hz).

MS (ES+) m/z 1687.4 [2M+Na]$^+$

Example 12

Preparation of Compounds 19 and 21

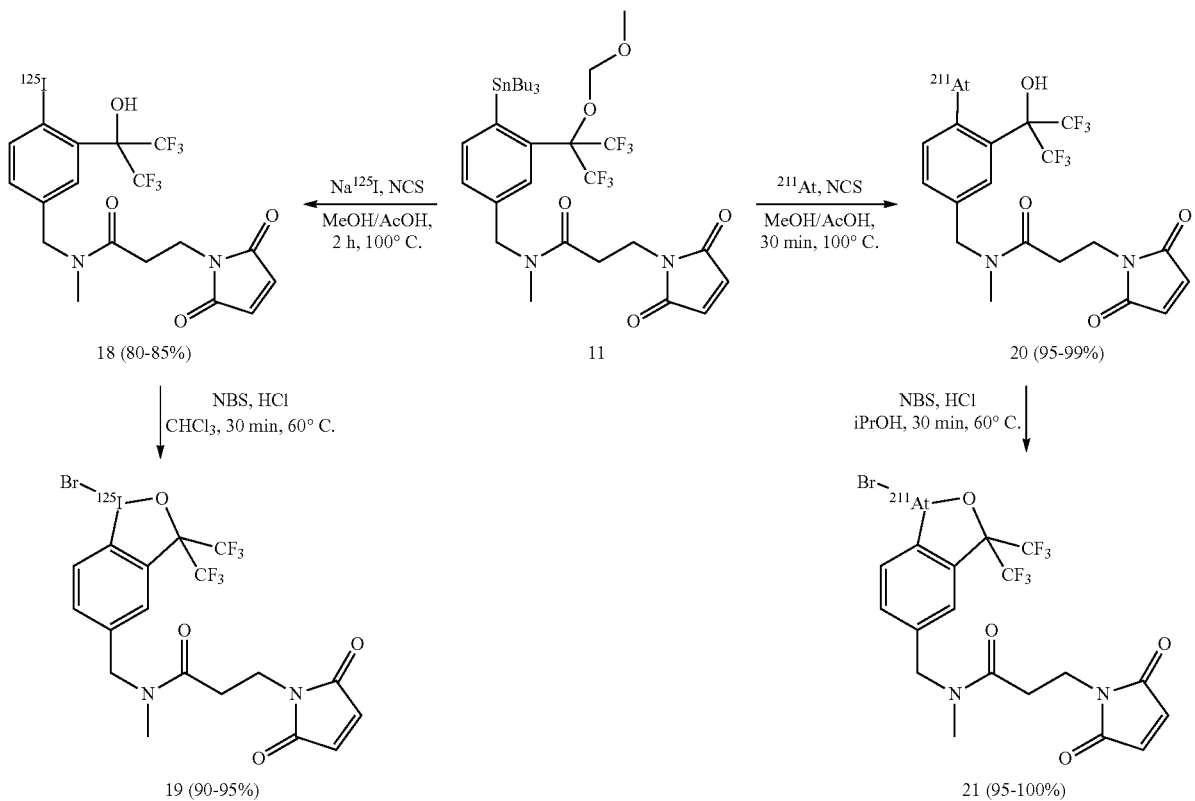

1. Preparation of Compound 18

[$^{125}$I]-N-(4-iodo-3-(1,1,1,3,3,3-hexafluoro-2-hydroxypropan-2-yl)benzyl)-N-(3-Maleimidopropionyl)-N-methylamide Compound 11 (of example 10) (237 nmol in 100 μL MeOH/AcOH 95/5), N-chlorosuccinimide (2.02 μmol in 100 μL MeOH/AcOH 95/5) and sodium [$^{125}$I] iodide (3.7 MBq in 1 μL NaOH 0.048N) were heated 2 h at 100° C. A TLC plate using chloroform/methanol (95/5) as eluant indicated a 80-85% radiochemical yield.

2. Preparation of Compound 19

[$^{125}$I]-N-((1-Bromo-1,3-dihydro-5-methyl-3,3-bis(trifluoromethyl)-1,2-benziodoxole)-N-(3-Maleimidopropionyl)-N-methylamide To 100 μL of the reaction mixture containing the compound 18 were added N-bromosuccinimide (847 μmol in 100 μL propan-2-ol). After heating 30 min at 50° C., a TLC plate using chloroform/methanol (95/5) as eluant indicated a 90-95% radiochemical yield.

3. Preparation of Compound 20

[$^{211}$At]-N-(4-astato-3-(1,1,1,3,3,3-hexafluoro-2-hydroxypropan-2-yl)benzyl)-N-(3-Maleimidopropionyl)-N-methylamide Compound 11 (10 nmol in 4 μL MeOH/AcOH 95/5), N-chlorosuccinimide (60 nmol in 3 μL MeOH/AcOH 95/5) and the astatine-211 activity (0.5 to 5 MBq in 50 μL MeOH) were heated 30 min at 100° C. A TLC plate using chloroform/methanol (95/5) as eluant indicated a 95-99% radiochemical yield.

4. Preparation of Compound 21

[$^{211}$At]-N-((1-Bromo-1,3-dihydro-5-methyl-3,3-bis(trifluoromethyl)-1,2-benzastatoxole)-N-(3-Maleimidopropionyl)-N-methylamide.

To 25 μL of the reaction mixture containing compound 20 were added N-bromosuccinimide (212 μmol in 25 μL propan-2-ol). After heating 30 min at 50° C., a TLC plate using chloroform/methanol (95/5) as eluant indicated a 95-100% radiochemical yield.

Example 13

Coupling of Compounds 20 and 21 to BSA

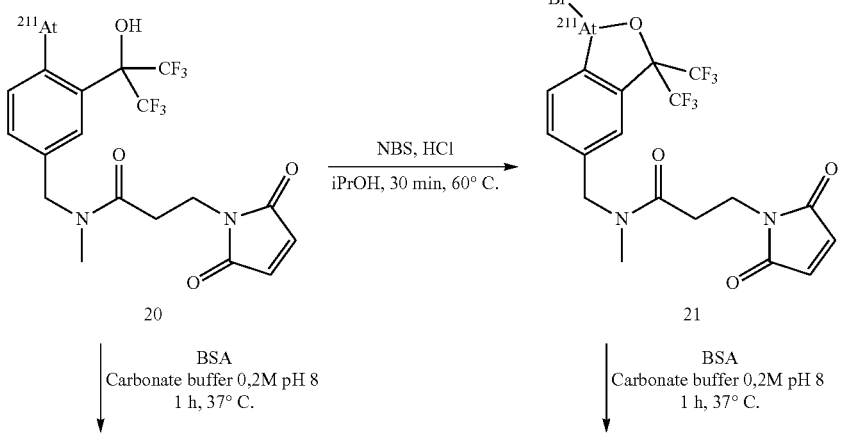

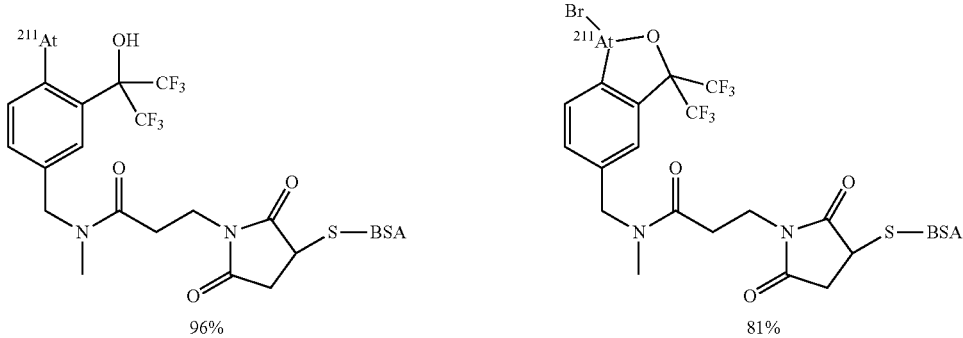

The disulfide bonds of the BSA were reduced before coupling. For that the BSA (5 mg/mL in PBS) was incubated with 20 equivalents of dithiothreitol for 1 h at room temperature. The reduced BSA was recovered with a 4 mg/mL concentration after elution through a PD-10 column with carbonate buffer (0.2 M, pH=8).

Coupling to Compound 20:

To 50 μL of the reaction mixture containing compound 20 was added 1M sodium sulfide (5 μL). The mixture was stirred 5 min at room temperature and the solvent was evaporated under gentle stream of nitrogen. 100 μL of the solution of reduced BSA were then added and the mixture was incubated for 1 h at 37° C. A ITLC-SG analysis eluted with 10% trichloroacetic acid indicated a 96% coupling yield. The crude product was eluted through a PD-10 column to yield the radiolabelled BSA with >99% purity.

Coupling to Compound 21:

To 100 μL of the reaction mixture containing compound 21 was evaporated under gentle stream of nitrogen. 100 μL of the solution of reduced BSA were then added and the mixture was incubated for 1 h at 37° C. A ITLC-SG analysis eluted with 10% trichloroacetic acid indicated a 81% coupling yield. The crude product was eluted through a PD-10 column to yield the radiolabelled BSA with >99 purity.

The invention claimed is:

1. A compound having formula (I):

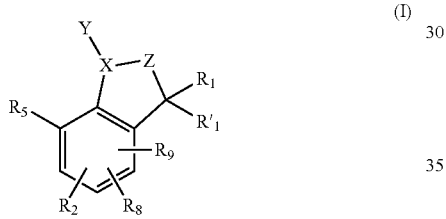

wherein:

X is a radioisotope selected from the group consisting of: $^{125}$I, $^{123}$I, $^{124}$I, $^{131}$I, and $^{211}$At;

$R_1$ and $R'_1$ are independently from each other selected from the group consisting of nitro, acyl, formyl, sulfonyl, cyano, chloride, bromide, fluoride, OAc, an alkyl group, OH, $NH_2$, or $R_1$ and $R'_1$ form together with the adjacent carbon atom carrying them a C=O group;

$R_2$ is selected from the group consisting of: H, an alkyl group, a functional group that binds a vector selected from the group consisting of maleimide, N-hydroxysuccinimide ester, tetrafluorophenyl ester, isothiocyanate, isocyanate, anhydride, alkyne, an azide group, and a functional group having targeting properties selected from the group consisting of biotin, hapten, an antibody, an antibody fragment, a peptide, a drug, and a nanocarrier;

$R_8$ and $R_9$ are independently selected from the group consisting of H, OH, $NH_2$, halogen, an alkyl group, an alkoxy group, an amine group, an amide group, and an ester group;

Z is a heteroatom selected from the group consisting of O and NH; and $R_5$ is H or a $C(R_6)(R_7)$ radical forming together with Y and X a five-membered heterocycle wherein:

when $R_5$=H, Y is an electron withdrawing group selected from the group consisting of: nitro, acyl, formyl, sulfonyl, trifluoromethyl, cyano, chloride, bromide, fluoride, and OAc; or when $R_5$=C($R_6$)($R_7$) radical forming together with Y and X a five-membered heterocycle, Y is selected from O and NH and $R_6$ and $R_7$ are as defined above for $R_1$ and $R'_1$.

2. The compound of claim 1, having formula (I-1):

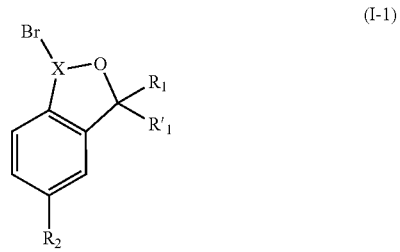

wherein X, $R'_1$, $R_1$ and $R_2$ are as defined in claim 1.

3. The compound of claim 1, having formula (I-2):

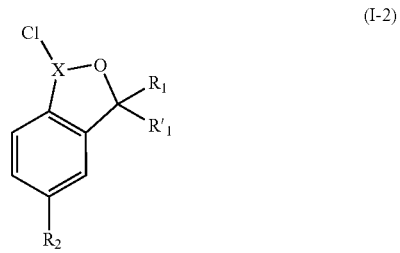

wherein X, $R'_1$, $R_1$ and $R_2$ are as defined in claim 1.

4. The compound of claim 1, wherein $R_1$ and $R'_1$ are selected from the group consisting of: a fluorinated alkyl, OH, $NH_2$, and nitro.

5. The compound of claim 1, wherein X is $^{125}$I.

6. The compound of claim 1, wherein X is $^{211}$At.

7. A method for the preparation of a compound having formula (I) according to claim 1, comprising reacting a halogenation agent with a compound of formula (III):

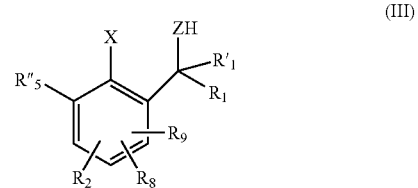

wherein:

X is a radioisotope selected from the group consisting of: $^{125}$I, $^{123}$I, $^{124}$I, $^{131}$I, and $^{211}$At;

$R_1$ and $R'_1$ are independently from each other selected from the group consisting of nitro, acyl, formyl, sulfonyl, cyano, chloride, bromide, fluoride, OAc, an alkyl group, OH, $NH_2$, or $R_1$ and $R'_1$ form together with the adjacent carbon atom carrying them a C=O group;

$R_2$ is selected from the group consisting of: H, alkyl group, a functional group that binds a vector selected from the group consisting of maleimide, N-hydroxysuccinimide ester, tetrafluorophenyl ester, isothiocyanate, isocyanate, anhydride, alkyne, an azide group, and a functional group having targeting properties selected from the group consisting of biotin, hapten, an antibody, an antibody fragment, a peptide, a drug, and a nanocarrier;

$R_8$ and $R_9$ are independently from each other selected from the group consisting of H, OH, $NH_2$, halogen, an alkyl group, an alkoxy group, an amine group, an amide group, and an ester group;

Z is a heteroatom selected from the group consisting of O and NH; and $R''_5$ is H or a $C(R_6)(R_7)(ZH)$ group, with $R_6$ and $R_7$ being as defined above for $R_1$ and $R'_1$.

8. A method for the preparation of a compound having formula (I-1) according to claim 2, comprising reacting a bromination agent selected from N-bromosuccinimide, $Br_2$, $CBr_4$, and $PBr_3$, with a compound of formula (III):

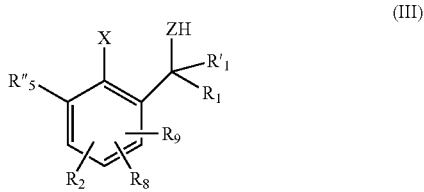

(III)

wherein:

X is a radioisotope selected from the group consisting of: $^{125}I$, $^{123}I$, $^{124}I$, $^{131}I$, and $^{211}At$;

$R_1$ and $R'_1$ are independently from each other selected from the group consisting of nitro, acyl, formyl, sulfonyl, cyano, chloride, bromide, fluoride, OAc, an alkyl group, OH, $NH_2$, or $R_1$ and $R'_1$ form together with the adjacent carbon atom carrying them a C=O group;

$R_2$ is selected from the group consisting of: H, alkyl group, a functional group that binds a vector selected from the group consisting of maleimide, N-hydrosuccinimide ester, tetrafluorophenyl ester, isothiocyanate, isocyanate, anhydride, alkyne, an azide group, and a functional group having targeting properties selected from the group consisting of biotin, hapten, an antibody, an antibody fragment, a peptide, a drug, and a nanocarrier;

$R_8$ and $R_9$ are independently from each other selected from the group consisting of H, OH, $NH_2$, halogen, an alkyl group, an alkoxy group, an amine group, an amide group, and an ester group;

Z is a heteroatom selected from the group consisting of O and NH; and $R''_5$ is H or a $C(R_6)(R_7)(ZH)$ group, with $R_6$ and $R_7$ being as defined above for $R_1$ and $R'_1$.

9. A method for the preparation of a compound having formula (I-2) according to claim 3, comprising reacting a chlorination agent selected from $Cl_2$, tBuOCl, $SO_2Cl_2$, $PCl_5$ and a mixture of hydrochloric acid and sodium hypochlorite, with a compound of formula (III):

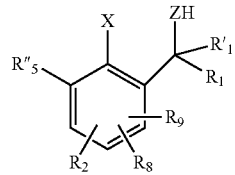

(III)

wherein:

X is a radioisotope selected from the group consisting of: $^{125}I$, $^{123}I$, $^{124}I$, $^{131}I$, and $^{211}At$;

$R_1$ and $R'_1$ are independently from each other selected from the group consisting of nitro, acyl, formyl, sulfonyl, cyano, chloride, bromide, fluoride, OAc, an alkyl group, OH, $NH_2$, or $R_1$ and $R'_1$ form together with the adjacent carbon atom carrying them a C=O group;

$R_2$ is selected from the group consisting of: H, alkyl group, a functional group that binds a vector selected from the group consisting of maleimide, N-hydrosuccinimide ester, tetrafluorophenyl ester, isothiocyanate, isocyanate, anhydride, alkyne, an azide group, and a functional group having targeting properties selected from the group consisting of biotin, hapten, an antibody, an antibody fragment, a peptide, a drug, and a nanocarrier;

$R_8$ and $R_9$ are independently from each other selected from the group consisting of H, OH, $NH_2$, halogen, an alkyl group, an alkoxy group, an amine group, an amide group, and an ester group;

Z is a heteroatom selected from the group consisting of O and NH; and $R''_5$ is H or a $C(R_6)(R_7)(ZH)$ group, with $R_6$ and $R_7$ being as defined above for $R_1$ and $R'_1$.

10. A pharmaceutical composition, comprising a compound of claim 1 and at least one pharmaceutically acceptable excipient.

11. The compound of claim 1, wherein at least one of $R_1$ and $R'_1$ is selected from the group consisting of nitro, acyl, formyl, sulfonyl, trifluoromethyl, cyano, chloride, bromide, fluoride, and OAc.

12. The compound of claim 1, wherein Y is an electron withdrawing group selected from the group consisting of bromide, chlorine, fluoride, and OAc.

13. The pharmaceutical composition claim 10, wherein said compound is coupled to a vector selected from biomolecules and nanocarrier compounds.

14. A method for treating or localizing tumors in a subject in need thereof, comprising
administering to said subject a therapeutically effective amount of a compound of claim 1.

15. The compound of claim 1, wherein the alkyl group of $R_1$ and $R'_1$ are selected from the group consisting of $CF_3$, $CF_2$—$CF_3$, and $CCl_3$.

* * * * *